United States Patent [19]

Kimura et al.

[11] Patent Number: 5,036,059

[45] Date of Patent: Jul. 30, 1991

[54] 1,4-DIHYDROPYRIDINE-3-CARBOXYLATE DERIVATIVES

[75] Inventors: Kiyoshi Kimura, Osaka; Iwao Morita, Kyoto, both of Japan

[73] Assignee: Nippon Shinyaku Company, Limited, Japan

[21] Appl. No.: 724,019

[22] Filed: Apr. 17, 1985

[30] Foreign Application Priority Data

Apr. 19, 1984 [JP] Japan .................................. 59-79560

[51] Int. Cl.$^5$ .................. A61K 31/675; C07D 211/92
[52] U.S. Cl. ........................................ 514/89; 546/15; 546/21

[58] Field of Search ....................... 546/21, 15; 514/89

[56] References Cited

U.S. PATENT DOCUMENTS

| | | | |
|---|---|---|---|
| 3,790,582 | 2/1974 | Demozay et al. | 546/25 |
| 4,044,141 | 8/1977 | Bossert et al. | 546/321 |
| 4,535,073 | 8/1985 | Kimura et al. | 514/89 |
| 4,576,934 | 3/1986 | Seto et al. | 514/89 |

Primary Examiner—Jane T. Fan
Attorney, Agent, or Firm—Rosenman & Colin

[57] ABSTRACT

1,4-Dihydropyridine-3-carboxylate derivatives are produced having vasodilating and hypotensive action.

60 Claims, No Drawings

1,4-DIHYDROPYRIDINE-3-CARBOXYLATE DERIVATIVES

The present invention is concerned with 1,4-dihydropyridine-3-carboxylates, pharmaceutically acceptable salts thereof, methods of production thereof, pharmaceutical compositions embodying said compounds as the active agent and methods of treatment utilizing said compounds and pharmaceutically acceptable salts thereof. The compounds and pharmaceutically acceptable salts of the present invention are useful for their vasodilating and hypotensive activity in humans and animals.

Dihydropyridine compounds having the structure set forth below are known in the art (see von K. Issleib, R. Wolff and M. Lengies: J. prakt. Chem. 318, 207–20 (1976). However, in the report by Issleib et al, production of only the two compounds set forth below was described and these two compounds were found not to exhibit any hypotensive activity:

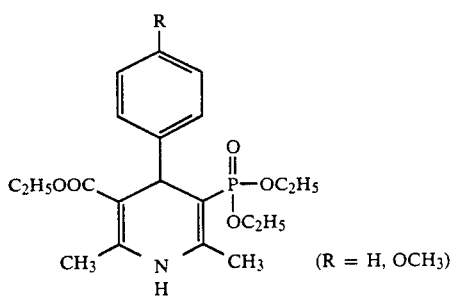

Nifedipine, which is dimethyl 2,6-dimethyl-4-(2-nitrophenyl)-1,4-dihydropyridine-3,5-dicarboxylate, is known to exhibit coronary vasodilating action and hypotensive action.

The present invention is based on the discovery that 1,4-dihydropyridine-3-carboxylates and pharmaceutically acceptable salts thereof which have various electronegative groups in the phenyl group linked to the 1,4-dihydropyridine and pharmaceutically acceptable salts thereof exhibit excellent vasodilating and hypotensive action.

More particularly, the compounds of the present invention are of the formula (I):

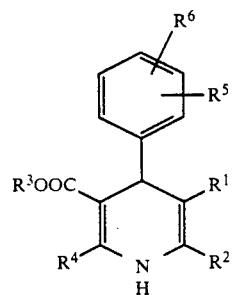

or a pharmaceutically acceptable salt thereof wherein $R^1$ is of the formula (II):

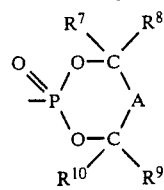

wherein A is

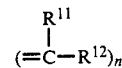

wherein n is an integer from 0 to 2 and $R^{11}$ and $R^{12}$ are the same or different and each is hydrogen, alkyl, alkoxycarbonyl, phenyl, alkoxy, alkoxyalkyl, phenoxy or aralkyloxy, or $R^{11}$ and $R^{12}$ together with the carbon atom to which they are attached form an alkylene group of 3 to 7 carbon atoms when n is 1 and when n is 2, both $R^{11}$ and $R^{12}$ are hydrogen, or two $R^{11}$ form a double bond while $R^{12}$ is hydrogen; $R^7$, $R^8$, $R^9$ and $R^{10}$ are the same or different and each is hydrogen or lower alkyl; $R^2$ is lower alkyl; $R^3$ is hydrogen; a hydrocarbon of 1 to 10 carbon atoms containing 0 to 4 unsaturated bonds unsubstituted or substituted by one or more substituents selected from the group consisting of alkoxy, aryl, aryloxy, aralkyloxy, amino, alkylamino, alkylthio, pyridyl, furfuryl and tetrahydrofurfuryl; a group of the formula

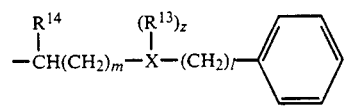

wherein X is nitrogen or oxygen; $R^{13}$ is lower alkyl or lower alkenyl and z is 1 when X is nitrogen and when X is oxygen, z is 0; $R^{14}$ is hydrogen, lower alkyl or phenyl unsubstituted or substituted by alkyl, preferably lower alkyl; l is an integer from 0 to 2; m is an integer from 1 to 4; a group of the formula

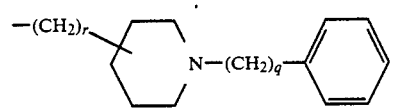

0041 wherein q is an integer from 0 to 2 and r is an integer from 0 to 2; or a group of the formula

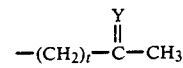

wherein t is 1 or 2 and Y is oxygen,

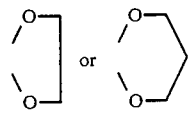

$R^4$ is lower alkyl; $R^5$ is hydrogen, nitro, cyano, trihalomethyl, dihalo-lower alkoxy, halo, azido, alkoxycarbonyl, aminocarbonyl, sulfamyl or alkylsulfonyl; and $R^6$ is hydrogen, nitro, cyano, trihalomethyl, dihalo-lower alkoxy, halo, azido, alkoxycarbonyl, aminocarbonyl, sulfamyl or alkylsulfonyl. When $R^3$ is hydrogen, it may be straight or branched chain, cyclic or a combination thereof.

According to one embodiment of the present invention, $R^{11}$ and $R^{12}$ are the same or different and each is hydrogen, lower alkyl, lower alkoxycarbonyl, phenyl, lower alkoxy, lower alkoxy lower alkyl, phenoxy or aralkyloxy wherein the alkyl moiety is of 1 to 4 carbon atoms; or $R^{11}$ and $R^{12}$ form an alkylene group together with the carbon atom to which they are attached of 3 to 7 carbon atoms when n is 1 or when n is 2, both $R^{11}$ and $R^{12}$ are hydrogen or two $R^{11}$ form a double bond and $R^{12}$ is hydrogen; $R^7$, $R^8$, $R^9$ and $R^{10}$ are the same or different and each is hydrogen or lower alkyl; $R^2$ is lower alkyl; $R^3$ is hydrogen, alkyl of 1 to 6 carbon atoms, alkenyl of 3 to 5 carbon atoms or cycloalkyl of 3 to 7 carbon atoms unsubstituted or substituted by one or two substituents selected from the group consisting of alkoxy of 1 to 4 carbon atoms, phenyl, phenoxy, benzyloxy, cycloalkyl of 3 to 7 carbon atoms, amino, alkylamino of 1 to 4 carbon atoms, alkylthio of 1 to 4 carbon atoms, pyridyl, furfuryl or tetrahydrofurfuryl; a group of the formula

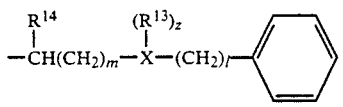

wherein X is nitrogen or oxygen; $R^{13}$ is alkyl of 1 to 4 carbon atoms; and z is 1 when X is nitrogen and when X is oxygen, z is 0; $R^{14}$ is hydrogen, alkyl of 1 to 4 carbon atoms or phenyl unsubstituted or substituted by alkyl of 1 to 4 carbon atoms; l is 0 to 2; m is 1 to 4; a group of the formula

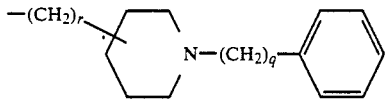

wherein q is 0 to 2 and r is 0 to 2; or a group of the formula

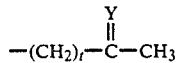

wherein t is 1 or 2; Y is oxygen,

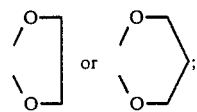

$R^4$ is alkyl of 1 to 4 carbon atoms; $R^5$ is hydrogen, nitro, cyano, trifluoromethyl, difluoromethoxy, halo, azido, alkoxycarbonyl of 1 to 4 carbon atoms, aminocarbonyl, sulfamyl or alkylsulfonyl of 1 to 4 carbon atoms; and $R^6$ is hydrogen, nitro, cyano, trifluoromethyl, difluoromethoxy, halo, azido, alkoxycarbonyl of 1 to 4 carbon atoms, aminocarbonyl, sulfamyl or alkylsulfonyl of 1 to 4 carbon atoms.

According to a further embodiment of the present invention, $R^1$ is 3-oxo-2,4-dioxa-3-phosphaspiro [5.5]undecan-3-yl or 2-oxo-1,3,2-dioxaphosphorinan-2-yl unsubstituted or substituted by one or more lower alkyl moieties; $R^2$ is alkyl of 1 to 4 carbon atoms; $R^3$ is alkyl of 1 to 5 carbon atoms or 2-(N-benzyl-N-lower alkylamino)-lower alkyl; $R^4$ is alkyl of 1 to 4 carbon atoms; $R^5$ is nitro, halo, trihalomethyl or dihaloalkoxy; and $R^6$ is hydrogen or halo.

According to a further embodiment of the present invention, $R^1$ is 3-oxo-2,4-dioxa-3-phosphorinaspiro [5.5]undecan-3-yl or 2-oxo-1,3,2-dioxaphosphorinan-2-yl unsubstituted or substituted by one or two alkyl moieties of 1 to 3 carbon atoms; $R^2$ is methyl, ethyl, propyl or isopropyl; $R^3$ is alkyl of 1 to 4 carbon atoms or 2-(N-benzyl-N-methylamino)ethyl; $R^4$ is methyl, ethyl, propyl or isopropyl; $R^5$ is nitro, chloro, trifluoromethyl or difluoromethoxy; and $R^6$ is hydrogen or chloro.

According to a further embodiment of the present invention, $R^1$ is 3-oxo-2,4-dioxa-3-phosphorinaspiro [5.5]undecan-3-yl or 2-oxo-1,3,2-dioxaphosphorinan-2-yl unsubstituted or substituted by methyl, ethyl or isopropyl at the 5-position; $R^2$ methyl; $R^3$ is methyl, ethyl or 2-(N-benzyl-N-methylamino)ethyl; $R^4$ is methyl; $R^5$ is nitro, chloro, trifluoromethyl or difluoromethoxy at the 2- or 3-position; and $R^6$ is hydrogen or 2-chloro.

According to a further embodiment of the present invention, $R^1$ is 2-oxo-1,3,2-dioxaphosphorinan-2-yl unsubstituted or substituted by 5-methyl; $R^2$ is methyl; $R^3$ is methyl or ethyl; $R^4$ is methyl; $R^5$ is nitro or trifluoromethyl at the 2- or 3-position; and $R^6$ is hydrogen.

Representative substituents for $R^1$ include the following:

2-oxo-1,3,2-dioxaphosphorinan-2-yl; 4-methyl-2-oxo-1,3,2-dioxaphosphorinan-2-yl; 5-methyl-2-oxo-1,3,2-dioxaphosphorinan-2-yl; 5-ethyl-2-oxo-1,3,2-dioxaphosphorinan-2-yl; 2-oxo-5-n-propyl-1,3,2-dioxaphosphorinan-2-yl; 5-isopropyl-2-oxo-1,3,2-dioxaphosphorinan-2-yl; 5-isobutyl-2-oxo-1,3,2-dioxaphosphorinan-2-yl; 2-oxo-5-phenyl-1,3,2-dioxaphosphorinan-2-yl; 5-methoxy-2-oxo-1,3,2-dioxaphosphorian-2-yl; 5-ethoxy-2-oxo-1,3,2-dioxaphosphorinan-2-yl; 5-benzyloxy-2-oxo-1,3,2-dioxaphosphorinan-2-yl; 2-oxo-5-phenoxy-1,3,2-dioxaphosphorinan-2-yl; 5,5-dimethyl-2-oxo-1,3,2-dioxaphosphorinan-2-yl; 5,5-diethyl-2-oxo-1,3,2-dioxaphosphorinan-2-yl; 2-oxo-5,5-di-n-propyl-1,3,2-dioxaphosphorinan-2-yl; 5,5-dimethoxycarbonyl-2-oxo-1,3,2-dioxaphosphorinan-2-yl; 5,5-diethoxycarbonyl-2-oxo-1,3,2-dioxaphosphorinan-2-yl; 4,6-dimethyl-2-oxo-1,3,2-dioxaphosphorinan-2-yl; 4(R),6(R)-dimethyl-2-oxo-1,3,2-dioxaphosphorinan-2-yl; 4,4,6-trimethyl-2-oxo-1,3,2-dioxaphosphorinan-2-yl; 4,4,6,6-tetramethyl-2-oxo-1,3,2-dioxaphosphorinan-2-yl; 2-oxo-1,3,2-dioxaphospholan-2-yl; 4,5-dimethyl-2-oxo-1,3,2-dioxaphospholan-2-yl; 2-oxo4,4,5,5-tetramethyl-1,3,2-dioxaphospholan-2-yl; 2-oxo-1,3,2-dioxaphosphepan-2-yl; 4,7-dimethyl-2-oxo-1,3,2-dioxaphosphepan-2-yl; 2-oxo-4,7-dihydro-1,3,2-dioxaphosphepin-2-yl; 7-oxo-6,8-dioxa-7-phosphaspiro (3,5)nonan-7-yl; 8-oxo-7,9-dioxa-8-phosphaspiro(4,5)decan-8-yl; and 3-oxo-2,4-dioxa-3-phosphaspiro(5,5)undecan-3-yl.

Representative moieties for $R^2$ include lower alkyls such as methyl, ethyl and propyl.

Representative moieties for $R^3$ include aliphatic hydrocarbons such as methyl, ethyl, n-propyl, isopropyl, n-butyl, isobutyl, sec-butyl, tert-butyl, n-pentyl, isopentyl, sec-pentyl, neopentyl, tert-pentyl, 1,2-dimethylpropyl, n-hexyl and isohexyl.

Representative unsaturated hydrocarbons for $R^3$ are those of 3 to 5 carbon atoms including allyl, crotyl, beta-methallyl, 1-ethyl-2-propenyl, propargyl, 1-methyl-2-butenyl, 3-butenyl, 3-methyl-3-butenyl, 3-butynyl and phenyl.

Cyclic hydrocarbons representative of $R^3$ are those of 3 to 7 carbon atoms such as cyclopropyl, cyclobutyl, cyclopentyl, cyclohexyl, cycloheptyl and cycloalkylalkyl including cyclopropylmethyl, cyclobutylmethyl and cyclopentylmethyl.

Representative alkoxyalkyl groups for $R^3$ include beta-methoxyethyl, beta-ethoxyethyl, beta-n-propoxyethyl, beta-isopropoxyethyl, 3-methyl-3-methoxybutyl, 1,3-dimethoxy-2-propyl and the like. Representative phenyl alkyl groups include benzyl and phenethyl. Representative phenylalkenyl groups include cinnamyl.

Other representative substituents for $R^3$ include 2-dimethylaminoethyl, 3-dimethylaminopropyl, 2-dimethylaminoethyl, 2-methylthioethyl, 2-ethylthioethyl, 2-propylthioethyl, tetrahydrofurfuryl, pyridylalkyls such as 2-pyridylmethyl, 3-pyridylmethyl, 4-pyridylmethyl, 2-(2-pyridyl)-ethyl, 3-(3-pyridyl)-propyl and the like.

Other representative examples of $R^3$ include 2-(N-benzyl-N-methylamilno)-ethyl, 2-(N-phenethyl-N-methylamino)-ethyl, 3-(N-benzyl-N-methylamino)-propyl, 4-(N-benzyl-N-methylamino)-butyl, 5-(N-benzyl-N-methylamino)-pentyl, 2-(N-benzyl-N-methylamino)-1-phenylethyl, and the like. Representative aralkyloxyalkyl groups include beta-benzyloxyethyl, beta-phenethyloxyethyl and the like. Examples of aryloxyalkyl groups included beta-phenoxyethyl groups which may be unsubstituted or substituted as above described.

Further examples of $R^3$ moieties include N-benzyl-4-piperidinyl, N-benzyl-3-piperidinyl, N-benzyl-2-piperidinyl, N-phenyl-4-piperidinyl, N-phenethyl-4-piperidinyl and the like.

Additional representative moieties for $R^3$ are 2,2-ethylenedioxypropyl, 2,2-trimethylenedioxypropyl, 3,3-ethylenedioxybutyl, 2-oxo-propyl, 3-oxo-butyl and the like.

Representative moieties for $R^4$ include lower alkyls such as methyl, ethyl and propyl.

In addition to the exemplified compounds, the following compounds are also representative of those of the present invention:

Methyl 4-(2-chlorophenyl)-2,6-dimethyl-5-(2-oxo-1,3,2-dioxaphosphorinan-2-yl)-1,4-dihydropyridine-3-carboxylate; methyl 4-(3-chlorophenyl)-2,6-dimethyl-5-(2-oxo-1,3,2-dioxaphosphorinan-2-yl)-1,4-dihydropyridine-3-carboxylate; methyl 2,6-dimethyl-5-(2-oxo-1,3,2-dioxaphosphorinan-2-yl)-4-(3-trifluoromethylphenyl)-1,4-dihydropyridine-3-carboxylate; methyl 2,6-dimethyl-4-(2-nitrophenyl)-5-(2-oxo-5-n-propyl-1,3,2-dioxaphosphorinan-2-yl)-1,4-dihydropyridine-3-carboxylate; methyl 5-(5-isobutyl-2-oxo-1,3,2-dioxaphosphorinan-2-yl)-2,6-dimethyl-4-(2-nitrophenyl)-1,4-dihydropyridine-3-carboxylate; methyl 2,6-dimethyl-4-(2-nitrophenyl)-5-(2-oxo-5,5-di-n-propyl-1,3,2-dioxaphosphorinan-2-yl)-1,4-dihydropyridine-3-carboxylate; methyl 2,6-dimethyl-4-(2-nitrophenyl)-5-(8-oxo-7,9-dioxa-8-phosphaspiro[4,5]decan-8-yl)-1,4-dihydropyridine-3-carboxylate; methyl 2,6-dimethyl-4-(2-nitrophenyl)-5-(2-oxo-5-phenyl-1,3,2-dioxaphosphorinan-2-yl)-1,4-dihydropyridine-3-carboxylate; methyl 2,6-dimethyl-4-(2-nitrophenyl)-5-(4-methyl-2-oxo-1,3,2-dioxaphosphorinan-2-yl)-1,4-dihydropyridine-3-carboxylate; methyl 2,6-dimethyl-4-(2-nitrophenyl)-5-(4,4,60trimethyl-2-oxo-1.3.2-dioxaphosphorinan-2-yl)-1,4-dihydropyridine-3-carboxylate; methyl 2,6-dimethyl-4-(2-nitrophenyl)-5-(4,4,6,6-tetramethyl-2-oxo-1,3,2-dioxaphosphorinan-2-yl)-1,4-dihydropyridine-3-carboxylate; methyl 2,6-dimethyl-5-(5-methoxy-2-oxo-1,3,2-dioxaphosphorinan-2-yl)-4-(2-nitrophenyl)-1,4-dihydropyridine-3-carboxylate; methyl 2,6-dimethyl-5-(5-ethoxy-2-oxo-1,3,2-dioxaphosphorinan-2-yl)-4-(2-nitrophenyl)-1,4-dihydropyridine-3-carboxylate; methyl 5-(5-benzyloxy-2-oxo-1,3,2-dioxaphosphorinan-2-yl)-2,6-dimethyl-4-(2-nitrophenyl)-1,4-dihydropyridine-3-carboxylate; methyl 2,6-dimethyl-4-(2-nitrophenyl)-5-(2-oxo-5-phenoxy-1,3,2-dioxaphosphorinan-2-yl)-1,4-dihydropyridine-3-carboxylate; methyl 5-(5,5-dimethoxycarbonyl-2-oxo-1,3,2-dioxaphosphorinan-2-yl)-2,6-dimethyl-4-(2-nitrophenyl)-1,4-dihydropyridine-3-carboxylate; methyl 2,6-dimethyl-5-(4,5-dimethyl-2-oxo-1,3,2-dioxaphospholan-2-yl)-4-(2-nitrophenyl)-1,4-dihydropyridine-3-carboxylate; methyl 2,6-dimethyl-4-(2-nitrophenyl)-5-(2-oxo-1,3,2-dioxaphospholan-2-yl)-1,4-dihydropyridine-3-carboxylate; methyl 2,6-dimethyl-4-(2-nitrophenyl)-5-(2-oxo-1,3,2-dioxaphosphepan-2-yl)-1,4-dihydropyridine-3-carboxylate; methyl 2,6-dimethyl-5-(4,7-dimethyl-2-oxo-1,3,2-dioxaphosphepan-2-yl)-4-(2-nitrophenyl)-1,4-dihydropyridine-3-carboxylate and the like.

The compounds of the present invention have asymetric carbon atom(s) and the present invention includes, therefore, optical isomers and mixtures thereof. In the case of racemic compounds where the racemic compound is the base, it is, if desired, treated with an optically active acid to carry out optical resolution and from the resultant salt, the optically active base of the present compound may be obtained. In the case where the racemic compound is an acid, it may be, if desired, treated with an optically active base and the desired optically active acid can be obtained by a similar way.

The compounds of the formula (I) of the present invention may be produced by the following methods:

Method 1

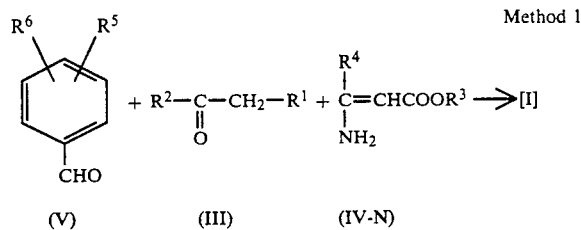

(V)   (III)   (IV-N)

wherein $R^1$, $R^2$, $R^3$, $R^4$, $R^5$ and $R^6$ are as above defined. Starting materials (V), (III) and (IV-N) are mixed within a molar ratio of 1:0.8:0.8 to 1:4:4 and, more preferably, in a ratio of 1:0.9:0.9 to 1:1.5:1.5. The reaction is carried out at room temperature to 150° C. and, more preferably, at 40°–100° C., in the presence or absence of an alcohol (such as methanol, ethanol, isopropanol and the like), an aromatic hydrocarbon (such as benzene, toluene and the like), a halogenated hydrocarbon (such as chloroform, carbon tetrachloride and the like), nonprotonic solvent (such as acetonitrile, N,N-dimethylformamide and the like), ether (such as tetrahydrofuran, dioxane and the like), water, etc.

Separation of the desired product from the reaction mixture is conducted by conventional methods such as, for example, concentration, extraction, column chromatography, recrystallization and the like.

The following additional methods may be used, using the same molar ratios, reaction solvents, temperatures and separation techniques as described above in Method 1.

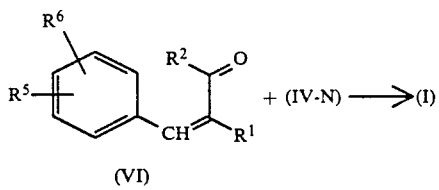

Method 2

(VI)

wherein $R^1$, $R^2$, $R^3$, $R^4$, $R^5$ and $R^6$ are as above defined.

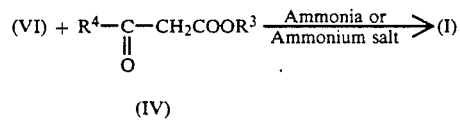

Method 3

(IV)

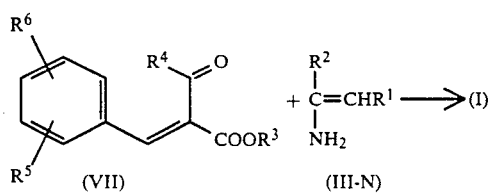

Method 4

(VII)    (III-N)

wherein $R^1$, $R^2$, $R^3$, $R^4$, $R^5$ and $R^6$ are as above defined.

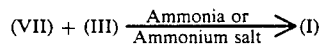

Method 5

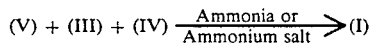

Method 6

The ammonium salts set forth above include ammonium acetate, ammonium carbonate, ammonium bicarbonate and the like.

Phosphonates represented by the general formula (III) used as starting materials are known in the art or can be manufactured by methods known in the art. For example, see A. N. Pudovik and V. P. Aver'yanoua: Zhur. Obshch. Doklady Akad. Nauk. S.S.S.R. 101, 889–92 (1955).

Beta-ketocarboxylates of the general formula (IV) used as starting materials are known in the art or can be manufactured by methods known in the art. For example, see D. Borrmann: "Umsetzung von Diketen mit Alkoholen, Phenolen und Mercaptanen" in Houben-Weyl, Methoden der organischen Chemie, Vol. VII 4, 230 (1968); Y. Oikawa, K. Sugano and O Yonemitsu: J. Org. Chem. 43, 2087 (1978).

Enamino esters of the formula (IV-N) used as starting materials are known in the art or can be manufactured by methods known in the art. For example, see A. C. Cope et al: J. Am. Chem. Soc. 67, 1017 (1945).

Enamino esters of the formula (III-N) used as starting materials may be manufactured by the same method as those of formula (IV-N).

Aromatic aldehydes of the formula (V) used as starting materials are known in the art and may be manufactured by conventional methods known in the art. For example, see E. Mosettig: Organic Reactions, VII, pg. 218 (1954).

Benzylidene derivatives of the formula (VI) used as starting materials may be manufactured by methods known in the art. For example, see A. N. Pudoruk, G. E. Yastrebova and V. I. Nikitina: Zh. Obshch. Khim. 37, 510–11(1967) and R. Wolff und M. Lengies: J. prakt. Chem. 318, 207–20 (1976). In the examples given below, the manufacture of these starting materials will be described in detail.

Benzylidene derivatives of the formula (VII) used as starting materials are known in the art or may be manufactured by methods known in the art. For example, see G. Jones: "The Knoevenagel Condensation" in Organic Reactions, Vol. XV, pg. 204 (1967).

The compounds of the present invention and their pharmaceutically acceptable salts show little toxicity and marked coronary vasodilating, hypotensive and other vasodilating actions. They have been found to be useful in the treatment of circulatory diseases such as hypertension, cardiac insufficiency, arrhythmia, angina pectoris, myocardial infarction, cerebral vessel disturbance, peripheral circulatory insufficiency and the like. When compared with nifedipine and diltiazem which are compounds known to be useful for the treatment of such diseases, the compounds of the present invention exhibit a weaker action on the heart muscle, more characteristic action on the coronary vessel and hypotensive action characterized by a slower onset and a longer duration of action.

Compounds representative of the present invention were tested for their coronary vasodilating and hypotensive action as compared with diltiazem. The results are set forth below:

Test Methods and Results (a) Coronary vasodilating action

Constant pressure perfusion samples of guinea pig heart isolated by a method according to Langendorff were treated with the present invention compounds by administration via coronary artery and the effect was examined (Table 1).

With reference to coronary vasodilating action of diltiazem measured by the same method, the increasing rates in perfusion by administration of $10^{-7}$, $10^{-6}$ and $10^{-5}$ gram/heart were 4, 16 and 55%, respectively. It is, therefore apparent that the present invention compounds exhibit more excellent coronary vasodilating action.

(b) Hypotensive action

Blood pressure of femoral artery of rats (with normal blood pressure) under unanesthetized condition was measured directly using a pressure tranducer.

The present invention compounds were given orally at doses of 1, 3 and 10 mg/kg, and changes in blood pressure were continuously recorded. Percent decreases of mean blood pressure at the peak effect were calculated. The maximum changes in mean blood pressure (%) were shown as "hypotensive action" (Table 2).

Hypotensive action of diltiazem (which is a known hypotensive drug) measured by the same method at the doses of 3, 10 and 30 mg/kg were 0, 11.2 and 33.0%, respectively. Hypotensive action of the compound of Example 4 which is one of the most representative compounds of this invention was tested using spontaneously hypertensive rats and was compared with those of Nifedipine and Diltiazem hydrochloride. The method applied was that the drugs were orally given to the rats of which systolic arterial blood pressure were higher than 180 mmHg when it was measured plethysmographically using tail arteries. (Table 3)

It is, therefore, apparent that the present invention compounds exhibit very excellent hypotensive action. Two compounds represented by the formula (VIII) wherein R is hydrogen or methoxy) were subjected to the same test and found to exhibit no hypotensive action.

(c) Acute Toxicity

Toxicity of the present invention compounds are very weak. All $LD_{50}$ values measured were not less than 400 mg/kg by oral administration to rats.

TABLE 1

| Example Number | Perfusion Increasing Rate | |
|---|---|---|
| | $10^{-7}$ | $10^{-6}$ gram/heart |
| 3 | 10% | 18% |
| 6 | 10 | 52 |
| 8 | 11 | 33 |
| 10 | 12 | 22 |
| 11 | 11 | 53 |
| 12 | 14 | 67 |
| 17 | 10 | 23 |
| 20 | 10 | 32 |
| 22 | 21 | 31 |
| 24 | 12 | 41 |
| 29 | 34 | 59 |
| 30 | 13 | 26 |
| 32 | 24 | 77 |
| 34 | 13 | 38 |
| 37 | 22 | 26 |
| 39 | 12% | 31% |
| 40 | 29 | 82 |
| 43 | 12 | 56 |
| 45 | 10 | 29 |
| 46 | 12 | 19 |
| 48 | 13 | 35 |
| 49 | 14 | 34 |
| 50 | 15 | 46 |
| 52 | 10 | 62 |
| 53 | 16 | 25 |
| 56 | 55 | 75 |
| 57 | 11 | 17 |
| 59 | 24 | 33 |
| 62 | 19 | 70 |

TABLE 2

| Example Number | (% Decreases in Mean Blood Pressure [at peak effect]) | | |
|---|---|---|---|
| | 10 | 3 | 1 mg/kg |
| 2 | 50.1 | 39.2 | 18.4 |
| 3 | 20.9 | 11.1 | 8.2 |
| 4 | 41.9 | 39.0 | 42.6 |
| 5 | 46.2 | 43.3 | 39.7 |
| 7 | 31.4 | 18.4 | 12.7 |
| 8 | 37.1 | 15.5 | 8.1 |
| 9 | 40.4 | 12.9 | 12.7 |
| 17 | 47.0 | 36.8 | 24.8 |
| 18 | 45.5 | 42.7 | 15.7 |
| 22 | 18.4 | 10.4 | 7.3 |
| 26 | 43.8 | 37.1 | 28.7 |
| 28 | 33.9 | 26.6 | 16.5 |
| 32 | 30.5 | 21.2 | 7.8 |
| 50 | 47.2 | 44.3 | 42.3 |
| 51 | 45.4 | 43.0 | 21.1 |
| 52 | 42.8 | 37.2 | 18.4 |
| 53 | 49.7 | 45.4 | 24.5 |
| 59 | 35.1 | 29.1 | 7.1 |
| 62 | 48.3 | 37.4 | 10.6 |
| 64 | 41.5 | 16.5 | 6.9 |
| 68 | 45.8 | 41.7 | 13.0 |
| 76 | 40.2 | 35.0 | 10.5 |

TABLE 3

| | Control | Compd. of Ex. 4* | Nifedipine** | Diltiazem.HCl*** |
|---|---|---|---|---|
| Before administration | 192.8 ± 6.9 | 185.2 ± 5.4 (193.0 ± 6.5) | 194.8 ± 2.1 (189.0 ± 5.1) | 191.2 ± 5.4 |
| After administration | | | | |
| 0.5 hr | 193.3 ± 6.8 | 126.0 ± 3.9 (87.7 ± 4.9) | 139.3 ± 6.9 (112.8 ± 6.0) | 153.6 ± 5.4 |
| 1 hr | 196.2 ± 4.6 | 124.0 ± 3.3 (90.2 ± 6.3) | 161.3 ± 4.1 (125.8 ± 4.4) | 141.8 ± 10.8 |
| 2 hr | 192.5 ± 6.3 | 134.2 ± 4.3 (103.2 ± 7.3) | 183.5 ± 10.0 (148.7 ± 9.9) | 156.2 ± 8.8 |
| 3 hr | 188.7 ± 6.2 | 152.5 ± 4.0 (133.3 ± 5.3) | 188.3 ± 5.8 (176.8 ± 2.6) | 170.5 ± 4.8 |
| 5 hr | 186.3 ± 5.3 | 156.8 ± 8.3 (150.7 ± 7.7) | 187.2 ± 5.3 (183.8 ± 6.0) | 183.2 ± 2.8 |
| 8 hr | 186.7 ± 5.1 | 158.3 ± 7.2 (152.8 ± 6.5) | 190.9 ± 4.8 (188.5 ± 2.9) | 189.3 ± 4.6 |
| 12 hr | 188.3 ± 7.2 | 170.7 ± 5.4 (165.3 ± 6.1) | 190.3 ± 5.5 (190.0 ± 7.0) | 188.5 ± 2.0 |
| 24 hr | 190.5 ± 4.8 | 195.3 ± 5.9 (187.7 ± 7.5) | — (—) | — |

Doses in mg/kg (p.o.) are as follows: *0.3 (1.0); 1.0 (3.0); *30.

The present invention also includes pharmaceutical compositions utilizing a compound of the formula (I) or a pharmaceutically acceptable salt thereof in combination with a pharmaceutically acceptable carrier for administration to humans and animals for effecting vasodilating and hypotensive action. Such pharmaceutical compositions contain from 0.1 to 99.5%, preferably 0.5 to 90%, of active agent.

Examples of the carriers applicable are one or more of solid, semi-solid or liquid diluents, fillers and other pharmaceutical auxiliary agents. It is desired that the pharmaceutical preparations are administered as a unit dosage form. The present invention pharmaceutical preparations may be administered per os, into tissue, locally (such as via skin) or rectally. Of course the administration is conducted by a form suitable for each route. For instance, oral administration is especially preferred.

It is desired that the dose is regulated after considering the state of the patients such as age, body weight, etc., administration route, and the nature and degree of the disease but, usually, the range of 1 to 1000 mg, preferably 2 to 100 mg, of the present invention compound per adult per day is common. Of course, in some cases, it is sufficient even below the above range and, in other cases, even more dosage may be necessary. When large dose is given, it is desired that the compound is administered dividedly—i.e. several times a day.

Oral administration is carried out by a solid or liquid dose unit form such as, for example, pure powder, diluted powder, tablets, sugar coated tablets, capsules, granules, suspensions, liquid, syrups, drops, sublingual tablets and other forms.

Pure powder is manufactured by making active substance into suitable fine size.

Diluted powder is manufactured by making the active substance into suitable fine size and the mixed with similarly fine carriers such as starch, mannitol and other edible hydrocarbons and others. If necessary, seasoning agents, preservatives, dispersion agents, colouring agents, perfumes, and others may be mixed therewith.

Capsules are manufactured as follows. Thus, the pure powder or diluted powder in powdery form as above or the granules as illustrated in the entry of tablets are filled in outer capsules such as, for example, gelatine capsule. It is of course possible to mix the powdery substances with lubricants or fluidizing agents such as, for example, colloidal silica, talc, magnesium stearate, calcium stearate, solid polyethylene glycol and the like followed by conducting the filling operation. Addition of disintegrating agents or solubilizing agents such as, for example, carboxy methyl cellulose, carboxy methyl cellulose calcium, hydroxypropyl cellulose with low degree of substitution, calcium carbonate, sodium carbonate and the like is effective in improving the effectiveness of the pharmaceuticals when capsules are taken.

Finely powdered compound of the present invention may also be suspended and dispersed in vegetable oil, polyethylene glycol, glycerine, surface active agents, and the like and packed with gelatine sheets to afford soft capsules.

Tablets are manufactured by first preparing powdery mixture, then made into granules or slugs, mixed with disintegrating agents or lubricants, and then made into tablets.

Powdery mixtures are prepared by mixing a suitably pulverized substance with the above-given diluents or bases followed, if necessary, by mixing with combining agents (such as sodium carboxy methyl cellulose, alginates, gelatine, polyvinyl pyrrolidone, polyvinyl alcohol and the like), solubilization retarding agents (such as paraffine), reabsorbing agents (such as quaternary salts) and/or adsorbing agents (such as bentonite, kaolin, dicalcium phosphate and the like). Powdery mixtures may be made into granules by first wetting with combining agents such as syrup, starch paste, gum arabicum, cellulose solution or polymer solution followed by a compulsory passing through a sieve. Instead of granulating the powder as such, the powder may be first treated with a tablet machine and then pulverizing the obtained slugs of various forms to give granules.

Granules thus prepared are mixed with lubricants such as stearates, stearic acid, talc, mineral oil and others whereupon it is possible to prevent adherence each other. Such a lubricated mixture is then compressed to make tablets. Alternatively, the active substances are, without granulation and making into slugs, directly compressed into tablets after mixing with fluidizing inert carriers. Transparent or semitransparent protective coatings comprising closed shellac membrane, coatings of sugar or polymers, and brushing up coatings comprising waxes may also be used.

Other preparation forms for oral administration such as solutions, syrups, elixiers, and the like may also be in a dosage unit form in which its definite amount contains definite amount of the pharmaceutically active substance. Syrups are manufactured by dissolving a compound in a suitable aqueous solution of sweetening agent and perfumes. Elixiers are prepared by the use of non-toxic alcoholic carriers. Suspensions are prepared by dispersing the compound in non-toxic carriers. If necessary, solubilizing agents and emulsifying agents (such as ethoxylated isostearyl alcohols, polyoxyethylene sorbitol esters, etc), preservatives, seasoning agents (such as peppermint oil, saccharine, etc.) and others may also be added.

If necessary, dose unit forms for oral administration may be made into microcapsules. Said form may also be coated and embedded in polymers or wax so that prolongation of acting time or sustained released effect can be resulted.

Parenteral administration can be done by the use of liquidal dosage unit forms (such as solution or suspension) suitable for subcutaneous, intramuscular or intravenous injections. They are manufactured first by suspending or dissolving a definite amount of the compound in non-toxic liquid carriers suitable for each injection purpose such as aqueous or oily medium and then by sterilizing said suspension or solution. Alternatively, a definite amount of the compound is taken into vials and then the vial together with the content therein are sterilized and sealed. In order to make the substance dissolved or mixed immediately before administration, preliminary or auxiliary vials or carriers may be prepared in addition to pulverized or lyophilized effective constituent. In order to make the injection solution isotonic, non-toxic salt or a solution thereof may be added thereto. Further, stabilizers, preservatives, emulsifiers, and the like may be simultaneously applied.

Rectal administration can be conducted by the use of suppositories in which the compound is mixed with a lower melting solid (which is soluble or insoluble in water) such as, for example, polyethylene glycol, cacao butter, higher esters (such as myristyl palmitate) or a mixture thereof.

Pharmaceutical preparations of the present invention compounds may be combined with other pharmaceuticals such as, for example, nitrites, beta-blockers, diuretic hypotensive drugs, and the like and may be used jointly with them.

The method of use of the compounds and pharmaceutically acceptable salts of the present invention comprises administering to a human or animal in need thereof a therapeutically effective amount of a compound of the formula (I) or a pharmaceutically acceptable salt thereof, in combination with a pharmaceutically acceptable carrier.

Manufacture methods of the starting materials for the present invention compounds are given as follows under Reference Example. Then several examples concerning the manufacture of the present invention compounds follow. Of course, the present invention is not limited or restricted thereto.

REFERENCE EXAMPLE

A mixture of 10.0 grams of 2-acetonyl-2-oxo-1,3,2-dioxaphosphorinane and 8.48 grams of m-nitrobenzaldehyde was dissolved in 120 ml of toluene, 1.0 gram of piperidine and 2.0 grams of acetic acid were added as catalysts and the mixture was heated to reflux for 15 hours with a water-remover. After cooled, the crystals separated out were removed by filtration, the filtrate was washed with water, then with aqueous solution of sodium hydroxide, further with 20% sodium acid sulfite solution and finally with water, and the organic solvent layer was dried. The solvent was removed by evaporation in vacuo, the residue was purified by silica gel column chromatography, and 4.5 grams of 2-(1-(3-nitrobenzylidene)acetonyl)-2-oxo-1,3,2-dioxaphosphorinane was obtained as an EZ mixture. Recrystalized from ethyl acetate. M.p. 144°–145.5° C.

IR$\nu_{max}^{KBr}$(cm$^{-1}$) 1695, 1610, 1525, 1350, 1270, 1055.

Elementary analysis calculated for $C_{13}H_{14}NO_6P$: C 50.17, H 4.53, N 4.50; Found: 50.26, H 4.66, N 4.54%.

Similarly prepared were the following compounds:

2-(1-(2-Nitrobenzylidene)-acetonyl)-2-oxo-1,3,2-dioxaphosphorinane: m.p. 134°–143° C. (recrystallized from ethyl acetate).

2-(1-(2-Trifluoromethylbenzylidene)-acetonyl)-2-oxo-1,3,2-dioxaphosphorinane: pale brown oil. IR (film, cm$^{-1}$): 1700, 1320, 280, 1170, 1120, 1055, 965, 815, 770.

2-(1-(2-Difluoromethoxybenzylidene)-acetonyl)-2-oxo-1,3,2-dioxaphosphorinane: m.p. 85°–87° C. (recrystallized from ether-ethyl acetate).

2-(1-(2,3-Dichlorobenzylidene)-acetonyl)-2-oxo-1,3,2-dioxaphosphorinane: m.p. 93°–95° C. (recrystallized from ether-ethyl acetate).

EXAMPLE 1

(a) Into 80 ml of isopropanol were dissolved 5.5 grams of 2-(1-(3-nitrobenzylidene)-acetonyl)-2-oxo-1,3,2-dioxaphosphorinane and 2.1 grams of methyl 3-aminocrotonate and the mixture was heated to reflux for 10 hours. After the reaction, the reaction solution was concentrated in vacuo, the residue was made crystallized by addition of ethyl acetate, and crystals separated out were collected by filtration. The crude crystals were recrystallized from ethyl acetate to give 3.6 grams of methyl 2,6-dimethyl-4-(3-nitrophenyl)-5-(2-oxo-1,3,2-dioxaphosphorinan-2-yl)-1,4-dihydropyridine-3-carboxylate, m. p. 221°–3° C.

IR (KBr, cm$^{-1}$): 3290, 3230, 3110, 1710, 1650, 1535, 1505, 1350, 1250, 1220, 1100, 930, 850, 810.

NMR (CDCl$_3$, $\delta$): 1.72–1.82 (1H, m), 2.04–2.16 (1H, m), 2.33 (3H, s), 2.35 (3H, d, J=2.5 Hz), 3.67 (3H, s), 3.93–4.28 (2H, m), 4.40–4.60 (2H, m), 4.86 (1H, d, J=10.5 Hz), 6.21 (1H, d, J=5 Hz), 7.38 (1H, t, J=8 Hz), 7.63 (1H, d, J=8 Hz), 8.01 (1H, m), 8.10 (1H, t, J=2 Hz).

Elementary analysis calculated for $C_{18}H_{21}N_2O_7P$: C 52.95, H 5.18, N 6.86; Found: C 52.83, H 5.14, N 6.68%.

(b) 2-Acetonyl-2-oxo-1,3,2-dioxaphosphorinane (1.78 grams) was dissolved in 10 ml of methanol and ammonia gas was bubbled thereinto with ice cooling and stirring for ten minutes. The reaction solution was stirred at room temperature for 2 hours and methanol was removed by evaporation in vacuo. The residue was dissolved in 10 ml of anhydrous ethanol, 100 mg of sodium hydride (50% mineral oil) was added, the mixture was stirred for 10 minutes, then a mixture of 2.41 grams of methyl 2-(3-nitrobenzylidene)-acetoacetate and 1 gram of ammonium carbonate was added, and the mixture was heated to reflux for eight hours with stirring. The reaction solution was concentrated in vacuo, the residue was dissolved in ethyl acetate, the solution was washed with 5% aqueous solution of sodium hydroxide, then with water, the organic solvent layer was dried with magnesium sulfate, and concentrated in vacuo. The concentrate was purified by subjecting to a silica gel column chromatography to give 0.41 gram of methyl 2,6-dimethyl-4-(3-nitrophenyl)-5-(2-oxo-1,3,2-dioxaphosphorinan-2-yl)-1,4-dihydropyridine-3-carboxylate.

(c) 2-Acetonyl-2-oxo-1,3,2-dioxaphosphorinane (1.78 grams) was dissolved in 10 ml of methanol and ammonia gas was bubbled thereinto for ten minutes with stirring and ice cooling. The reaction solution was stirred at room temperature for two hours and methanol was removed therefrom by evaporation in vacuo. The residue was dissolved in 15 ml of anhydrous ethanol, 200 mg of sodium hydride (50% mineral oil) was added thereto, stirred for ten minutes, then 1.51 grams of 3-nitrobenzaldehyde, 1.16 grams of methyl acetoacetate, and 1 gram of ammonium carbonate were added thereto, and the mixture was heated to reflux for eight hours. Then the reaction solution was subjected to an after-treatment as same as in (b) to give 0.32 gram of methyl 2,6-dimethyl-4-(3-nitrophenyl)-5-(2-oxo-1,3,2-dioxaphosphorinan-2-yl)-1,4-dihydropyridine-3-carboxylate.

EXAMPLE 2

A mixture of 3.11 grams of 2-(1-(3-nitrobenzylidene)-acetonyl)-2-oxo-1,3,2-dioxaphosphorinane and 2.48 grams of 2-(N-benzyl-N-methylamino)ethyl 3-aminocrotonate was dissolved in 30 ml of isopropanol and the mixture was heated to reflux for eight hours. The reaction solution was concentrated in vacuo and the residue was purified by subjecting to a column chromatography (silica gel, n-hexane-ethyl acetate). The resulting pale yellow oil (3.8 grams) was crystallized with ether and recrystallized from a mixture of ethyl acetate and ether to give 3.2 grams of 2-(N-benzyl-N-methylamino)ethyl 2,6-dimethyl-4-(3-nitrophenyl)-5-(2-oxo-1,3,2-dioxaphosphorinan- 2-yl)-1,4-dihydropyridine-3-carboxylate, pale yellow crystals, m.p. 139°–40° C.

IR (KBr, cm$^{-1}$): 3290, 3220, 3100, 1695, 1645, 1530, 1505, 1350, 1250, 1230, 1050.

NMR (CDCl$_3\delta$): 1.68–1.80 (1H, m), 1.95–2.15 (1H, m), 2.21 (3H,s),2.32(3H,s 2.34 (3H, d, J=2.5Hz), 2.66 (2H, t, J=6.0 Hz), 3.51 (2H, s), 3.9–4.1 (2H, m), 4.20 (2H, t, J=6.0 Hz), 4.35–4.60 (2H, m), 4.89 (1H, d, J=10.5 Hz), 6.37 (1H, d, J=5Hz), 7.26 (5H, s), 7.3–7.4 (1H, m), 7.66 (1H, d, J=8Hz), 7.98 (1H, d, J=8Hz), 8.10 (1H, t, J=2 Hz).

Elementary analysis calculated for $C_{27}H_{32}N_3O_7P$: C 59.88, H 5.96, N 7.76; Found: C 59.80, H 6.10, N 7.68%.

EXAMPLE 3

N-Benzyl-4-piperidinyl 2,6-dimethyl-4-(3-nitrophenyl)-5-(2-oxo-1,3,2-dioxaphosphorinan-2-yl)-1,4-dihydropyridine-3-carboxylate.

The same reaction and after-treatment as in Example 2 were conducted and purification with column chromatography (silica gel, n-hexane-ethyl acetate) gave pale yellow oily product.

MS (m/e): M+567.

IR (film, cm$^{-1}$): 3300, 3220, 3100, 1690, 1645, 1530, 1500, 1350, 1235, 1090, 1055.

EXAMPLE 4

Methyl 2,6-dimethyl-4-(2-nitrophenyl)-5-(2-oxo-1,3,2-dioxaphosphorinan-2-yl)-1,4-dihydropyridine-3-carboxylate.

A mixture of 4.04 grams of 2-(1-(2-nitrobenzylidene)-acetonyl-2-oxo-1,3,2-dioxaphorinane and 1.61 grams of methyl 3-aminocrotonate in 80 ml of ethanol was heated to reflux for twenty hours. The reaction solution was concentrated in vacuo, to the residue was added 40 ml of ethyl acetate, the mixture was heated with stirring for 10 minutes, allowed to cool until room temperature, crystals separated out were collected by filtration, washed with ethyl acetate, and the resulting crude crystals were recrystallized from ethanol to give 3.6 grams of the title product, yellow crystals. m.p. 249°–51° C.

IR (KBr, cm$^{-1}$): 3280, 3200, 3080, 1690, 1650, 1630, 1530, 1505, 1350, 1250, 1230, 1060, 930, 820, 805.

NMR (CDCl$_3$, δ): 1.64–1.74 (2H, m), 2.27 (3H, s), 2.45 (3H, d, J=2.6 Hz), 3.57 (3H, s), 3.85–4.05 (2H, m), 4.20–4.70 (2H, m), 5.60 (1H, d, J=10.5Hz), 6.22 (1H, d, J =6Hz), 7.20–7.29 (1H, m), 7.40–7.56 (2H, m), 7.70 (1H, d, J=8.0 Hz).

Elementary analysis calculated for C$_{18}$H$_{21}$N$_2$O$_7$P: C 52.95, H 5.18, N 6.86; Found: C 52.81, H 5.24, N 6.81%.

EXAMPLE 5

Ethyl 2,6-dimethyl-4-(2-nitrophenyl)-5-(2-oxo-1,3,2-dioxaphosphorinan-2-yl)-1,4-dihydropyridine-3-carboxylate.

The same reaction and after-treatment as in Example 4 were carried out to give the title product, yellow crystals, m.p. 173°–5° (recrystallized from ethyl acetate).

IR (KBr, cm$^{-1}$): 3280, 3210, 3100, 1700, 1640, 1535, 1500, 1355, 1310, 1235, 1110, 1060.

NMR (CDCl$_3$, δ): 1.19 (3H, t, J=7Hz), 1.67–1.76 (2H, m), 2.26 (3H, s), 2.41 (3H, d, J=2Hz), 3.86–4.35 (6H, m), 5.68 (1H, d, J=10.5 Hz), 6.48 (1H, d, J=5Hz), 7.20–7.28 (1H, m), 7.40–7.56 (2H, m), 7.75 (1H, d-d, J=1.8 Hz).

Elementary analysis calculated for C$_{19}$H$_{23}$N$_2$O$_7$P: C 54.03, H 5.49, N 6.63; Found: C 53.83, H 5.57, N 6.68%.

The compound of Examples 6 to 74 are prepared in a manner analogous to the process described in Examples 1 to 5.

EXAMPLE 6

Isopropyl 2,6-dimethyl-4-(2-nitrophenyl)-5-(2-oxo-1,3,2-dioxaphosphorinan-2-yl)-1,4-dihydropyridine-3-carboxylate.

M.p. 159°–61° C.

Elementary analysis calculated for C$_{20}$H$_{25}$N$_2$O$_7$P: C 55.05, H 5.77, N 6.42; Found: C 55.06, H 5.90, N 6.40%.

The compound was produced from 2-[1-(2-nitrobenzylidene)acetonyl]-2-oxo-1,3,2-dioxaphosphorinane and isopropyl 3-aminocrotonate.

EXAMPLE 7

Methyl 2,6-dimethyl-5-(5,5-dimethyl-2-oxo-1,3,2-dioxaphosphorinan-2-yl)-4-(3-nitrophenyl)-1,4-dihydropyridine-3-carboxylate. M.p. 208°–9° C. Elementary analysis calculated for C$_{20}$H$_{25}$N$_2$O$_7$P: C 55.05, H 5.77, N 6.42; Found: C 55.08, H 5.76, N 6.33%.

EXAMPLE 8

Ethyl 2,6-dimethyl-5-(5,5-dimethyl-2-oxo-1,3,2-dioxaphosphorinan-2-yl)-4-(3-nitrophenyl-1)-1,4-dihydropyridine-3-carboxylate. M.p. 154°–6° C. Elementary analysis calculated for C$_{21}$H$_{27}$N$_2$O$_7$P: C 56.00, H 6.04, N 6.22; Found: C 56.33, H 6.06, N 5.91%.

EXAMPLE 9

2-(N-Benzyl-N-methylamino)-ethyl 2,6-dimethyl-5-(5,5-dimethyl-2-oxo-1,3,2-dioxaphosphorinan-2-yl)-4-(3-nitrophenyl)-1,4-dihydropyridine-3-carboxylate.

M.p. 125°–6° C. Elementary analysis calculated for C$_{29}$H$_{36}$N$_3$O$_7$P.½H$_2$O: C 60.20, H 6.45, N 7.26; Found: C 60.21, H 6.64, N 7.07%.

EXAMPLE 10

2-(N,N-Dimethylamino)ethyl 2,6-dimethyl-5-(5,5-dimethyl-2-oxo-1,3,2-dioxaphosphorinan-2-yl)-4-(3-nitrophenyl)-1,4-dihydropyridine-3-carboxylate. M.p. 96°–8° C. Elementary analysis calculated for C$_{23}$H$_{32}$N$_3$O$_7$P: C 55.98, H 6.54, N 8.52; Found: C 55.66, H 6.78, N 8.38%.

EXAMPLE 11

2-n-Propoxyethyl 2,6-dimethyl-5-(5,5-dimethyl-2-oxo-1,3,2-dioxaphosphorinan-2-yl)-4-(3-nitrophenyl)-1,4-dihydropyridine-3-carboxylate. M.p. 163°–4° C. Elementary analysis calculated for C$_{24}$H$_{33}$N$_2$O$_8$P: C 56.69, H 6.54, N 5.51; Found: C 56.60, H 6.78, N 5.52%.

EXAMPLE 12

2-Benzyloxyethyl 2,6-dimethyl-5-(5,5-dimethyl-2-oxo-1,3,2-dioxaphosphorinan-2-yl)-4-(3-nitrophenyl)-1,4-dihydropyridine-3-carboxylate. M.p. 166°–7° C. Elementary analysis calculated for C$_{28}$H$_{33}$N$_2$O$_8$P: C 60.43, H 5.98, N 5.03; Found: C 60.10, H 5.98, N 5.03%.

EXAMPLE 13

2-Methoxy-1-methoxymethylethyl 2,6-dimethyl-5-(5,5-dimethyl-2-oxo-1,3,2-dioxaphosphorinan-2-yl)-4-(3-nitrophenyl)-1,4-dihydropyridine-3-carboxylate.

M.p. 174°–5° C. Elementary analysis calculated for C$_{24}$H$_{33}$N$_2$O$_9$P: C 54.96, H 6.34, N 5.34; Found: C 54.61, H 6.55, N 5.17%.

EXAMPLE 14

2-Pyridylmethyl 2,6-dimethyl-5-(5,5-dimethyl-2-oxo-1,3,2-dioxaphosphorinan-2-yl)-4-(3-nitrophenyl)-1,4-dihydropyridine-3-carboxyalte. M.p. 195°–6° C. Elementary analysis calculated for C$_{25}$H$_{28}$N$_3$O$_7$P.½H$_2$O: C 57.47, H 5.59, N 8.04; Found: C 57.65, H 5.53, N 8.10%.

EXAMPLE 15

Methyl 2,6-dimethyl-5-(5,5-dimethyl-2-oxo-1,3,2-dioxaphosphorinan-2-yl)-4-(2-nitrophenyl)-1,4-dihydropyridine-3-carboxylate. M.p. 249°–51° C. Elementary analysis calculated for C$_{20}$H$_{25}$N$_2$O$_7$P: C 55.05, H 5.77, N 6.42; Found: C 54.83, H 5.88, N 6.38%.

EXAMPLE 16

Methyl 2,6-dimethyl-5-(4,6-dimethyl-2-oxo-1,3,2-dioxaphosphorinan-2-yl)-4-(3-nitrophenyl)-1,4-dihydropyridine-3-carboxylate. M.p. 198°–200° C. Elementary analysis calculated for C$_{20}$H$_{25}$N$_2$O$_7$P: C 55.05, H 5.77, N 6.42; Found: C 54.81, H 5.72, N 6.19%.

EXAMPLE 17

2-(N-Benzyl-N-methylamino)-ethyl 2,6-dimethyl-5-(4,6-dimethyl-2-oxo-1,3,2-dioxaphosphorinan-2-yl)-4-(3-nitrophenyl)-1,4-dihydropyridine-3-carboxylate. Oily substance. MS (m/e): M+569.

EXAMPLE 18

Methyl 2,6-dimethyl-5-(4,6-dimethyl-2-oxo-1,3,2-dioxaphosphorinan-2-yl)-4-(2-nitrophenyl)-1,4-dihydropyridine-3-carboxylate. M.p. 125°–35° C. Elementary analysis calculated for C$_{20}$H$_{25}$N$_2$O$_7$P: C 55.05, H 5.77, N 6.42; Found: C 54.83, H 5.88, N 6.38.

EXAMPLE 19

Methyl 2,6-dimethyl-5-[4(R),6(R)-dimethyl-2-oxo-1,3,2-dioxaphosphorinan-2-yl]-4-(3-nitrophenyl)-1,4-dihydropyridine-3-carboxylate. M.p. 225°–6° C.$[\alpha]_D^{23} = -24.67$ (c=0.762, ethanol). Elementary analysis calculated for $C_{20}H_{25}N_2O_7P$: C 55.05, H 5.77, N 6.42; Found: C 54.98, H 5.80, N 6.43%.

EXAMPLE 20

2-(N-Benzyl-N-methylamino)-ethyl 2,6-dimethyl-5-[4(R),6(R)-dimethyl-2-oxo-1,3,2-dioxaphosphorinan-2-yl]-4-(3-nitrophenyl)-1,4-dihydropyridine-3-carboxylate. Pale yellow oily substance. MS (m/e): M+569. $[\alpha]_D = 9.40$ (c=1.340, ethanol).

EXAMPLE 21

Methyl 5-(5,5-diethyl-2-oxo-1,3,2-dioxaphosphorinan-2-yl)-2,6-dimethyl-4-(3-nitrophenyl)-1,4-dihydropyridine-3-carboxylate. M.p. 223°–4° C. Elementary analysis calculated for $C_{22}H_{29}N_2O_7P$: C 56.89, H 29, N 6.03; Found: C 56.77, H6.6, N 5.99%.

EXAMPLE 22

2-(N-Benzyl-N-methylamino)-ethyl 5-(5,5-diethyl-2-oxo-1,3,2-dioxaphosphorinan-2-yl)-2,6-dimethyl-4-(3-nitrophenyl)-1,4-dihydropyridine-3-carboxylate. M.p. 171°–2° C. Elementary analysis calculated for $C_{31}H_{40}N_3O_7P$: C 62.30, H 6.75, N 7.03; Found: C 62.30, H 6.95, N 6.99%.

EXAMPLE 23

Ethyl 5-(5,5-diethyl-2-oxo-1,3,2-dioxaphosphorinan-2-yl)-2,6-dimethyl-4-(3-nitrophenyl)-1,4-dihydropyridine-3-carboxylate. M.p. 151°–2° C. Elementary analysis calculated for $C_{23}H_{31}N_2O_7P$: C 57.74, H 6.53, N 5.85; Found: C 57.90, H 6.85, N 5.80%.

EXAMPLE 24

Methyl 5-(5,5-diethyl-2-oxo-1,3,2-dioxaphosphorinan-2-yl)-2,6-dimethyl-4-(2-nitrophenyl)-1,4-dihydropyridine-3-carboxylate. M.p. 234°–5° C. Elementary analysis calculated for $C_{22}H_{29}N_2O_7P$: C 56.89, H 6.29, N 6.03; Found: C 56.70, H 6.39, N 6.04%.

EXAMPLE 25

Ethyl 5-(5,5-diethyl-2-oxo-1,3,2-dioxaphosphorinan-2-yl)-2,6-dimethyl-4-(2-nitrophenyl)-1,4-dihydropyridine-3-carboxylate. M.p. 201°–3° C. Elementary analysis calculated for $C_{23}H_{31}N_2O_7P$: C 57.74, H 6.53, N 5.85; Found: C 57.67, H 6.64, N 5.83%.

EXAMPLE 26

Methyl 5-(5-(5-methyl-2-oxo-1,3,2-dioxaphosphorinan-2-yl)-2,6-dimethyl-4-(3-nitrophenyl)-1,4-dihydropyridine-3-carboxylate. M.p. 177°–9° C. Elementary analysis calculated for $C_{19}H_{23}N_2O_7P$: C 54.03, H 5.49, N 6.63; Found: C 53.72, H 5.63, N 6.45%. The compound was produced from 5-methyl 2-[1-(3-nitrobenzylidene)-acetonyl]-2-oxo-,3,2-dioxaphosphorinane and methyl 3-aminocrontonate.

EXAMPLE 27

2-(N-Benzyl-N-methylamino)-ethyl 2,6-dimethyl-5-(5-methyl-2-oxo-1-3,2-dioxaphosphorinan-2-yl)-4-(3-nitrophenyl)-1,4-dihydropyridine-3-carboxylate. M.p. 156°–8° C. Elementary analysis calculated for $C_{28}H_{34}N_3O_7P$: C 60.54, H 6.17, N 7.56; Found: C 60.24, H 6.41, N 7.39%.

EXAMPLE 28

Methyl 5-(5-ethyl-Z-oxo-1,3,2-dioxaphosphorinan-2-yl)-2,6-dimethyl-4-(3-nitrophenyl)-1,4-dihydropyridine-3-carboxylate. M.p. 122°–3° C. Elementary analysis calculated for $C_{20}H_{25}N_2O_7P$: C 55.05, H 5.78, N 6.42; Found: C 54.66, H 5.83, N 6.43%.

EXAMPLE 29

2-(N-Benzyl-N-methylamino)-ethyl 5-(5-ethyl-2-oxo-1,3,2-dioxaphosphorinan-2-yl)-2,6-dimethyl-4-(3-nitrophenyl)-1,4-dihydropyridine-3-carboxylate. M.p. 145°–6° C. Elementary analysis calculated for $C_{29}H_{36}N_3O_7P$: C 61.15, H 6.37, N 7.38; Found: C 60.95, H 6.48, N 7.28%.

EXAMPLE 30

Methyl 5-(5-ethyl-2-oxo-1,3,2-dioxaphosphorinan-2-yl)-2,6-dimethyl-4-(2-nitrophenyl)-1,4-dihydropyridine-3-carboxylate. M.p. 163°–4° C. Elementary analysis calculated for $C_{20}H_{25}N_2O_7P \cdot \frac{1}{4}H_2O$: C 54.48, H 5.83, N 6.35; Found: C 54.61, H 5.91, N 6.38%.

EXAMPLE 31

Methyl 2,6-dimethyl-4-(3-nitrophenyl)-5-(5-isopropyl-2-oxo-1,3,2-dioxaphosphorinan-2-yl)-1,4-dihydropyridine-3-carboxylate. M.p. 94°–6° C. Elementary analysis calculated for $C_{21}H_{27}N_2O_7P \cdot \frac{1}{4}H_2O$: C 55.44, H 6.09, N 6.16; Found: C 55.55, H 6.18, N 6.15%.

EXAMPLE 32

Ethyl 2,6-dimethyl-4-(3-nitrophenyl)-5-(5-isopropyl-2-oxo-1,3,2-dioxaphosphorinan-2-yl)-1,4-dihydropyridine-3-carboxylate. M.p. 127°–30° C. Elementary analysis calculated for $C_{22}H_{29}N_2O_7P$: C 56.89, H 6.29, N 6.03; Found: C 56.84, H 6.31, N 6.03%. The compound was produced from 5-isopropyl-2-[1-(3-nitrobenzylidene)-acetonyl-2-oxo-1,3,2-dioxaphosphorinane and ethyl 3-aminocrotonate.

EXAMPLE 33

2-(N-Benzyl-N-methylamino)-ethyl 2,6-dimethyl-5-(5-isopropyl-2-oxo-1,3,2-dioxaphosphorinan-2-yl)-4-(3-nitrophenyl)-1,4-dihydropyridine-3-carboxylate. M.p. 161°–2° C. Elementary analysis calculated for $C_{30}H_{38}N_3O_7P$: C 61.74, H 6.56, N 7.20; Found: C 61.54, H 6.75, N 7.08%.

EXAMPLE 34

Methyl 2,6-dimethyl-5-(5-isopropyl-2-oxo-1,3,2-dioxaphosphorinan-2-yl)-4-(2-nitrophenyl)-1,4-dihydropyridine-3-carboxylate. M.p. 182°–4° C. Elementary analysis calculated for $C_{21}H_{27}N_2O_7P \cdot \frac{1}{2}H_2O$: C 54.90, H 6.14, N 6.10; Found: C 54.75, H 6.24, N 6.11%.

EXAMPLE 35

Ethyl 2,6-dimethyl-5-(5-isopropyl-2-oxo-1,3,2-dioxaphosphorinan-2-yl)-4-(2-nitrophenyl)-1,4-dihydropyridine-3-carboxylate. M.p. 156°–8° C. Elementary analysis calculated for $C_{22}H_{29}N_2O_7P$: C 56.89, H 6.29, N 6.03; Found: C 56.88, H 6.45, N 5.87%.

EXAMPLE 36

Methyl 2,6-dimethyl-4-(3-nitrophenyl)-5-(7-oxo-6,8-dioxa-7-phosphaspiro(3,5)nonan-7-yl)-1,4-dihydropyridine-3-carboxylate. M.p. 217°–19° C. Elementary analysis calculated for $C_{21}H_{25}N_2O_7P$: C 56.25, H 5.62, N 6.25; Found: C 56.02, H 5.81, N 6.11%.

EXAMPLE 37

2-(N-Benzyl-N-methylamino)-ethyl-2,6-dimethyl-4-(3-nitrophenyl)-5-(7-oxo-6,8-dioxa-7-phosphaspiro(3,5-)nonan-7-yl)-1,4-dihydropyridine-3-carboxylate. M.p. 188°–9° C. Elementary analysis calculated for $C_{30}H_{36}N_3O_7P$: C 61.95, H 6.24, N 7.22; Found: C 61.83, H 6.39, N 7.22%.

EXAMPLE 38

Methyl 2,6-dimethyl-4-(2-nitrophenyl)-5-(7-oxo-6,8-dioxa-7-phosphoaspiro(3,5)nonan-7-yl)-1,4-dihydropyridine-3-carboxylate. M.p. 174°–7° C. Elementary analysis calculated for $C_{21}H_{25}N_2O_7P \cdot \frac{1}{4}H_2O$: C 55.69, H 5.68, N 6.19; Found: C 55.73, H 5.75, N 6.11%.

EXAMPLE 39

Ethyl 2,6-dimethyl-4-(2-nitrophenyl)-5-(7-oxo-6,8-dioxa-7-phosphaspiro(3,5)nonan-7-yl)-1,4-dihydropyridine-3-carboxylate. M.p. 125°–8° C. Elementary analysis calculated for $C_{22}H_{27}N_2O_7P \cdot \frac{1}{4}iso\text{-}Pr_2O$: C 57.84, H 6.30, N 5.74; Found: C 57.77, H 6.54, N 5.53%.

EXAMPLE 40

Methyl 2,6-dimethyl-4-(3-nitrophenyl)-5-(3-oxo-2,4-dioxa-3-phosphoaspiro(5,5)undecan-3-yl)-1,4-dihydropyridine-3-carboxylate. M.p. 199°–200° C. Elementary analysis calculated for $C_{23}H_{29}N_2O_7P$: C 57.98, H 613, N 5.88; Found: C 57.80, H 6.23, N 5.81%.

EXAMPLE 41

2-(N-Benzyl-N-methylamino)-ethyl 2,6-dimethyl-4-(3-nitrophenyl)-5-(3-oxo-2,4-dioxa-3-phosphaspiro(5,5)undecan-3-yl)-1,4-dihydropyridine-3-carboxylate. M.p. 198°–200° C. Elementary analysis calculated for $C_{32}H_{40}N_3O_7P$: C 63.04, H 6.61, N 6.89; Found: C 63.06, H 6.79, N 6.77%.

EXAMPLE 42

Methyl 2,6-dimethyl-4-(2-nitrophenyl)-5-(3-oxo-2,4-dioxa-3-phosphaspiro(5,5)undecan-3-yl)-1,4-dihydropyridine-3-carboxylate. M.p. 136°–7° C. Elementary analysis calculated for $C_{23}H_{29}N_2O_7P$: C 57.98, H 6.13, N 5.88; Found: C 57.70, H 6.41, N 5.53%.

EXAMPLE 43

Ethyl 2,6-dimethyl-4-(2-nitrophenyl)-5-(3-oxo-2,4-dioxa-3-phosphaspiro(5,5)undecan-3-yl)-1,4-dihydropyridine-3-carboxylate. M.p. 138°–40° C. Elementary analysis calculated for $C_{24}H_{31}N_2O_7P$: C 58.77, H 6.37, N 5.71; Found: C 58.74, H 6.50, N 5.67%. The compound was produced from 3-[1-(2-nitrobenzylidene)-acetonyl]-30-oxo-2,4-dioxa-3-phosphaspiro(5,5)undecane and ethyl 3-aminocrotonate.

EXAMPLE 44

Methyl 5-(5,5-diethoxycarbonyl-2-oxo-1,3,2-dioxaphosphorinan-2-yl)-2,6-dimethyl-4-(3-nitrophenyl)-1,4-dihydropyridine-3-carboxylate. M.p. 216°–17° C. Elementary analysis calculated for $C_{24}H_{29}N_2O_{11}P$: C 52.18, H 5.29, N 5.07; Found: C 2.05, H 5.46, N 5.06%.

EXAMPLE 45

2-(N-Benzyl-N-methylamino)-ethyl 5-(5,5-diethoxycarbonyl-2-oxo-1,3,2-dioxaphosphorinan-2-yl)-2,6-dimethyl-4-(3-nitrophenyl)-1,4-dihydropyridine-3-carboxylate. M.p. 142°–3° C. Elementary analysis calculated for $C_{33}H_{40}N_3O_{11}P$: C 57.81, H 5.88, N 6.13; Found: C 57.67, H 6.12, N 6.06%.

EXAMPLE 46

Methyl 5-(5,5-diethoxycarbonyl-2-oxo-1,3,2-dioxaphosphorinan-2-yl)-2,6-dimethyl-4-(2-nitrophenyl)-1,4-dihydropyridine-3-carboxylate. M.p. 198°–9° C. Elementary analysis calculated for $C_{24}H_{29}N_2O_{11}P$: C 52.18, H 5.29, N 5.07; Found: C 52.12, H 5.36, N 5.09%.

EXAMPLE 47

Methyl 2,6-dimethyl-4-(3-nitrophenyl)-5-(2-oxo-4,4,5,5-tetramethyl-1,3,2-dioxaphospholan-2-yl)-1,4-dihydropyridine-3-carboxylate. M.p. 236°–7° C. Elementary analysis calculated for $C_{21}H_{27}N_2O_7P$: C 56.00, H 6.04, N 6.22; Found: C 56.04, H 6.24, N 6.22%.

EXAMPLE 48

2-(N-Benzyl-N-methylamino)-ethyl 2,6-dimethyl-4-(3-nitrophenyl)-5-(2-oxo-4,4,5,5-tetramethyl-1,3,2-dioxaphospholan-2-yl)-1,4-dihydropyridine-3-carboxylate. M.p. 186°–8° C. Elementary analysis calculated for $C_{30}H_{38}N_3O_7P$: C 61.74, H 6.56, N 7.20; Found: C 61.71, H 6.69, N 7.12%.

EXAMPLE 49

2-n-Propoxyethyl 2,6-dimethyl-4-(3-nitrophenyl)-5-(2-oxo-4,4,5,5-tetramethyl-1,3,2-dioxaphospholan-2-yl)-1,4-dihydropyridine-3-carboxylate. M.p. 169°–70° C. Elementary analysis calculated for $C_{25}H_{35}N_2O_8P$: C 57.47, H 6.75, N 5.36; Found: C 57.37, H 6.95, N 5.37%.

EXAMPLE 50

Methyl 2,6-dimethyl-5-(2-oxo-1,3,2-dioxaphosphorinan-2-yl)-4-(2-trifluoromethylphenyl)-1,4-dihydropyridine-3-carboxylate. M.p. 209°–11° C. Elementary analysis calculated for $C_{19}H_{21}F_3NO_5P$: C 52.91, H 4.91, N 3.25; Found: C 52.94, H 5.15, N 3.16%. The compound was produced from 2-[1-(2-trifluoromethyl-benzylidene)-acetonyl]-2-oxo-1,3,2-dioxaphosphoriane and methyl 3-aminocrotonate.

EXAMPLE 51

Ethyl 2,6-dimethyl-5-(2-oxo-1,3,2-dioxaphosphorinan-2-yl)-4-(2-trifluoromethylphenyl)-1,4-dihydropyridine-3-carboxylate. M.p. 175°–7° C. Elementary analysis calculated for $C_{20}H_{23}F_3NO_5P$: C 53.94, H 5.21, N 3.14; Found: C 53.77, H 5.30, N 3.27%.

EXAMPLE 52

2-(N-Benzyl-N-methylamino)-ethyl 2,6-dimethyl-(5-(2-oxo-1,3,2-dioxaphosphorinan-2-yl)-4-(2-trifluoromethylphenyl)-1,4-dihydropyridine-3-carboxylate. Pale yellow oil. MS (m/e) M+564. The compound was produced from 2-[1-(2-trifluoromethyl-benzylidene)-acetoxy]-2-oxo-1,3,2-dioxaphosphorinane and 2-(N-benzyl-N-methylamino)ethyl 3-aminocrotonate.

EXAMPLE 53

Methyl 4-(2-difluoromethoxyphenyl)-2,6-dimethyl-5-(2-oxo-1,3,2-dioxaphosphorinan-2-yl)-1,4-dihydropyridine-3-carboxylate. M.p. 192°–3° C. Elementary analysis calculated for $C_{19}H_{22}F_2NO_6P$: C 53.15, H 5.16, N 3.26; Found: C 53.15, H 5.28, N 3.25.

EXAMPLE 54

Ethyl 4-(2-difluoromethoxyphenyl)-2,6-dimethyl-5-(2-oxo-1,3,2-dioxaphosphorinan-2-yl)-1,4-dihydropyridine-3-carboxylate. M.p. 191°–2° C. Elementary analysis calculated for $C_{20}H_{24}F_2NO_6P$: C 54.18, H 5.46, N 3.16; Found: C 54.12, H 5.65, N 3.14%.

EXAMPLE 55

2-(N-Benzyl-N-methylamino)-ethyl 4-(2-difluoromethoxyphenyl)-2,6-dimethyl-5-(2-oxo-1,3,2-dioxaphosphorinan-2-yl)-1,4-dihydropyridine-3-carboxylate. Pale brown oil. MS (m/e): M+562.

EXAMPLE 56

Methyl 4-(2,3-dichlorophenyl)-2,6-dimethyl-5-(2-oxo-1,3,2-dioxaphosphorinan-2-yl)-1,4-dihydropyridine-3-carboxylate. M.p. 275°–7° C. Elementary analysis calculated for $C_{18}H_{20}Cl_2NO_5P$: C 50.02, H 4.66, N 3.24; Found: C 50.00, H 4.74, N 3.18%.The compound was produced from 2-[1-(2,3-dichlorobenzylidene)-acetonyl]-2-oxo-1,3,2-dioxaphosphorinane and methyl 3-aminocrotonate.

EXAMPLE 57

Ethyl 4-(2,3-dichlorophenyl)-2,6-dimethyl-5-(2-oxo-1,3,2-dioxaphosphorinan-2-yl)-1,4-dihydropyridine-3-carboxylate. M.p. 265°–7° C. Elementary analysis calculated for $C_{19}H_{22}Cl_2NO_5P$: C 51.14, H 4.97, N 3.14; Found: C 51.01, H 4.95, N 3.11%.

EXAMPLE 58

Methyl 4-(2,3-dichlorophenyl)-2,6-dimethyl-5-(5,5-dimethyl-2-oxo-1,3,2-dioxaphosphorinan-2-yl)-1,4-dihydropyridine-3-carboxylate. M.p. 167°–8° C. Elementary analysis calculated for $C_{20}H_{24}C_{12}NO_5P$: C 52.19, H 5.26, N 3.04; Found: C 52.21, H 5.31, N 3.12%.

EXAMPLE 59

2-(N-Benzyl-N-methylamino)-ethyl 4-(2,3-dichlorophenyl)-2,6-dimethyl-5-(5,5-dimethyl-2-oxo-1,3,2-dioxaphosphorinan-2-yl)-1,4-dihydropyridine-3-carboxylate. M.p. 197°–8° C. Elementary analysis calculated for $C_{29}H_{35}Cl_2N_2O_5P$: C 58.69, H 5.94, N 4.72; Found: C 58.53, H 6.04, N 4.61%.

EXAMPLE 60

Methyl 2,6-dimethyl-5-(5,5-dimethyl-2-oxo-1,3,2-dioxaphosphorinan-2-yl)-4-(2-trifluoromethylphenyl)-1,4-(dihydropyridine-3-carboxylate. M.p. 210°–12° C. Elementary analysis calculated for $C_{21}H_{25}F_3NO_5P$: C 54.90, H 5.49, N 3.09; Found: C 54.91, H 5.58, N 3.08%.

EXAMPLE 61

Ethyl 2,6-dimethyl-5-(5,5-dimethyl-2-oxo-1,3,2-dioxaphosphorinan-2-yl)-4-(2-trifluoromethylphenyl)-1,4-dihydropyridine-3-carboxylate. M.p. 223°–5° C. Elementary analysis calculated for $C_{22}H_{27}F_3NO_5P$: C 55.82, H 5.75, N 2.96; Found: C 55.94, H 5.89, N 2.97%.

EXAMPLE 62

2-(N-Benzyl-N-methylamino)-ethyl 2,6-dimethyl-5-(5,5-dimethyl-2-oxo-1,3,2-dioxaphosphorinan-2-yl)-4-(2-trifluoromethylphenyl)-1,4-dihydropyridine-3-carboxylate. Pale brown oil. MS (m/e): M[30]592. The compound was produced from 5,5-dimethyl-2-[1-(2-trifluoromethylbenzylidene)acetonyl]-2-oxo-1,3,2-dioxaphosphorinane and 2 (N-benzyl-N-methylamino)-ethyl 3-amino.

EXAMPLE 63

Methyl 4-(2-difluoromethoxyphenyl)-2,6-dimethyl)-5-(5,5-dimethyl-2-oxo-1,3,2-dioxaphosphorinan-2-yl)-1,4-dihydropyridine-3-carboxylate. M.p. 217°–18° C. Elementary analysis calculated for $C_{21}H_{26}F_2NO_6P$: C 55.14, H 5.73, N 3.06; Found: C 55.31, H 5.91, N 3.02%.

EXAMPLE 64

2-(N-Benzyl-N-methylamino)-ethyl 4-(2-difluoromethoxyphenyl)-2,6-dimethyl-5-(5,5-dimethyl-2-oxo-1,3,2-dioxaphosphorinan-2-yl)-1,4-dihydropyridine-3-carboxylate. Pale yellow oil. MS (m/e): M+590. The compound was produced from 5,5-dimethyl-2-[1-(2-difluoromethoxybenzylidene)acetonyl]-2-oxo-1,3,2-dioxaphosphorinane and 2-(N-benzyl-N-methylamino)ethyl 3-aminocrotonate.

EXAMPLE 65

Ethyl 2,6-dimethyl-5-(4,6-dimethyl-2-oxo-1,3,2-dioxaphosphorinan-2-yl)-4-(2-nitrophenyl)-1,4-dihydropyridine-3-carboxylate. M.p. 228°–30° C. Elementary analysis calculated for $C_{21}H_{27}N_2O_7P$: C 56.00, H 6.04, N 6.22; Found: C 56.05, H 6.08, N 6.17%.

EXAMPLE 66

Methyl 2,6-dimethyl-4-(2-nitrophenyl)-5-(2-oxo-4,7-dihydro-1,3,2-dioxaphosphepin -2-yl)-1,4-dihydropyridine-3-carboxylate. M.p. 221°–2.5° C. Elementary analysis calculated for $C_{19}H_{21}N_2O_7P$: C 54.29, H 5.04, N 6.66; Found: C 54.33, H 5.04, N 6.59%.

EXAMPLE 67 tert-Butyl 2,6-dimethyl-4-(2-nitrophenyl)-5-(2-oxo-1,3,2-dioxaphosphorinan-2-yl)-1,4-dihydropyridine-3-carboxylate. M.p. 120°–4° C. Elementary analysis calcualted for $C_{21}H_{27}N_2O_7P$: C 56.00, H 6.04, N 6.22; Found: C 55.93, H 6.13, N 6.21%.

EXAMPLE 68

Cyclopropylmethyl 2,6-dimethyl-4-(2-nitrophenyl)-5-(2-oxo-1,3,2-dioxaphosphorinan-2-yl)-1,4-dihydropyridine-3-carboxylate. M.p. 206°–8° C. Elementary analysis calculated for $C_{21}H_{25}N_2O_7P$: C 56.25, H 5.62, N 6.25; Found: C 56.31, H 5.56, N 6.32%.

EXAMPLE 69

Cyclopropylmethyl 2,6-dimethyl-5-(2-oxo-1,3,2-dioxaphosphorinan-2-yl)-4-(2-trifluoromethylphenyl)-1,4-dihydropyridine-3-carboxylate. M.p. 225°–5.5° C. Elementary analysis calculated for $C_{22}H_{25}F_3NO_5P$: C 56.05, H 5.35, N 2.97; Found: C 56.02, H 5.51, N 2.98%.

EXAMPLE 70

2,2-Ethylenedioxypropyl 2,6-dimethyl-4-(2-nitrophenyl)-5-(2-oxo-1,3,2-dioxaphosphorinan-2-yl)-1,4-dihydropyridine-3-carboxylate. M.p. 126°–7.5° C. Elementary analysis calculated for $C_{22}H_{27}N_2O_9P$: C 53.44, H 5.50, N 5.67; Found: C 53.06, H 5.37, N 5.67%.

EXAMPLE 71

2,2-Ethylenedioxypropyl 2,6-dimethyl-5-(2-oxo-1,3,2-dioxaphosphorinan-2-yl)-4-(2-trifluoromethylphenyl)-1,4-dihydropyridine-3-carboxylate. M.p. 188°–9.5° C. Elementary analysis calculated for $C_{23}H_{27}F_3NO_7P$: C 53.39, H 5.26, N 2.71; Found: C 53.57, H 5.28, N 2.70%.

EXAMPLE 72

Benzyl 2,6-dimethyl-5-(2-oxo-1,3,2-dioxaphosphorinan-2-yl)-4-(2-trifluoromethylphenyl)-1,4-dihydropyridine-3-carboxylate. M.p. 197°-8° C. Elementary analysis calculated for $C_{25}H_{25}F_3NO_5P$: C 59.17, H 4.97, N 2.76; Found: C 59.24, H 5.05, N 2.67%.

EXAMPLE 73

Cyclopentyl 2,6-dimethyl-5-(2-oxo-1,3,2-dioxaphosphorinan-2-yl)-4-(2-trifluoromethylphenyl)-1,4-dihydropyridine-3-carboxylate. M.p. 236°-8° C. Elementary analysis calculated for $C_{23}H_{27}F_3NO_5P$: C 56.91, H 5.61, N 2.89; Found: C 56.72, H 5.70, N 2.79%.

EXAMPLE 74

Allyl 2,6-dimethyl-5-(2-oxo-1,3,2-dioxaphosphorinan-2-yl)-4-(2-trifluoromethylphenyl)-1,4-dihydropyridine-3carboxylate. M.p. 192°-3° C. Elementary analysis calculated for $C_{21}H_{23}F_3NO_5P$: C 55.15, H 5.07, N 3.06; Found: C 55.55, H 5.17, N 3.04%.

EXAMPLE 75

2-Oxopropyl 2,6-dimethyl-4-(2-nitrophenyl)-5-(2-oxo-1,3,2-dioxaphosphorinan-2-yl)-1,4-dihydropyridine-3-carboxylate.

2,2-Ethylenedioxypropyl 2,6-dimethyl-4-(2-nitrophenyl)-5-(2-oxo-1,3,2-dioxaphosphorinan-2-yl)-1,4-dihydropyridine-3-carboxylate (2.3 grams) was heated to reflux for 6 hours in 20 ml of ethanol containing 2.5 ml of 10% hydrochloric acid. The solvent was evaporated therefrom in vacuo, the residue was dissolved in methylene chloride, the solution was dried with magnesium sulphate, and the solvent was evaporated therefrom. The residue was subjected to silica gel column chromatography to purify whereupon 1.6 grams of the title compound, pale yellow noncrystalline powder.

IR (KBr, cm$^{-1}$): 3300, 3225, 3100, 1735, 1705, 1650, 1535, 1505, 1360, 1240, 1110, 1055, 930.

Elementary analysis calculated for $C_{20}H_{23}N_2O_8P$: C 53.34, H 5.15, N 6.22; Found: C 53.34, H 5.43, N 5.97%.

EXAMPLE 76

2-Oxopropyl 2,6-dimethyl-5-(2-oxo-1,3,2-dioxaphosphorinan-2-yl)-4-(2-trifluoromethylphenyl)-1,4-dihydropyridine-3-carboxylate.

2,2-Ethylenedioxypropyl 2,6-dimethyl-5-(2-oxo-1,3,2-dioxaphosphorinan-2-yl)-4-(2-trifluoromethylphenyl)-1,4-dihydropyridine-3-carboxylate (2.5 grams) was subjected to the same reaction and after-treatment as in Example 75 to give 1.88 grams of the title compound, colourless non-crystalline powder.

IR (KBr, cm$^{-1}$): 3280, 3220, 3100, 1735, 1700, 1640, 1500, 1310, 1230, 1150, 1100, 1050.

Elementary analysis calculated for $C_{21}H_{23}F_3NO_6P$: C 53.28, H 4.90, N 2.96; Found: C 53.47, H 5.24, N 2.84%.

What we claim is:

1. A compound of the formula (I):

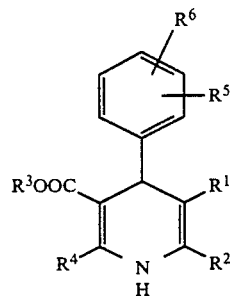

or a pharmaceutically acceptable salt thereof wherein $R^1$ is of the formula (II):

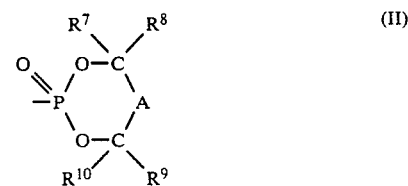

wherein A is

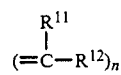

wherein n is an integer from 0 to 2 and $R^{11}$ and $R^{12}$ are the same or different and each is hydrogen, alkyl, alkoxycarbonyl, phenyl, alkoxy, alkoxyalkyl, phenoxy or aralkyloxy, or $R^{11}$ and $R^{12}$ together with the carbon atom to which they are attached form an alkylene group of 3 to 7 carbon atoms when n is 1 and when n is 2, both $R^{11}$ and $R^{12}$ are hydrogen, or two $R^{11}$ form a double bond while $R^{12}$ is hydrogen; $R^7$, $R^8$, $R^9$ and $R^{10}$ are the same or different and each is hydrogen or lower alkyl; $R^2$ is lower alkyl; $R^3$ is hydrogen; a hydrocarbon of 1 to 10 carbon atoms containing 0 to 4 unsaturated bonds unsubstituted or substituted by one or more substituents selected from the group consisting of alkoxy, aryl, aryloxy, aralkyloxy, cycloalkyl, amino, alkylamino, alkylthio, pyridyl, furfuryl and tetrahydrofurfuryl; a group of the formula

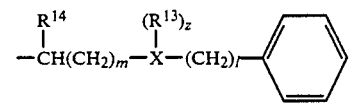

wherein X is nitrogen or oxygen; $R^{13}$ is lower alkyl or lower alkenyl and z is 1 when X is nitrogen and when X is oxygen, z is 0; $R^{14}$ is hydrogen, lower alkyl or phenyl unsubstituted or substituted by alkyl; l is an integer from 0 to 2; m is an integer from 1 to 4; a group of the formula

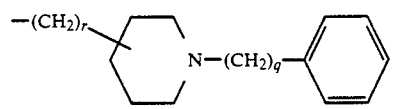

wherein q is an integer from 0 to 2 and r is an integer from 0 to 2; or a group of the formula

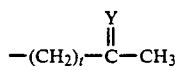

wherein t is 1 or 2 and Y is oxygen,

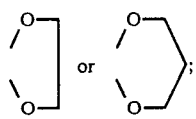

$R^4$ is lower alkyl; $R^5$ is hydrogen, nitro, cyano, trihalomethyl, dihalo-lower alkoxy, halo, azido, alkoxycarbonyl, aminocarbonyl, sulfamyl or alkylsulfonyl; and $R^6$ is hydrogen, nitro, cyano trihalomethyl, dihalo-lower alkoxy, halo, azido, alkoxycarbonyl, aminocarbonyl, sulfamyl or alkylsulfonyl.

2. A compound according to claim 1 or a pharmaceutically acceptable salt thereof wherein $R^{11}$ and $R^{12}$ are the same or different and each is hydrogen, lower alkyl, lower alkoxycarbonyl, phenyl, lower alkoxy, lower alkoxy lower alkyl, phenoxy or aralkyloxy wherein the alkyl moiety is of 1 to 4 carbon atoms; or $R^{11}$ and $R^{12}$ form an alkylene group together with the carbon atom to which they are attached of 3 to 7 carbon atoms when n is 1 or when n is 2, both $R^{11}$ and $R^{12}$ are hydrogen or two $R^{11}$ form a double bond and $R^{12}$ is hydrogen; $R^7$, $R^8$, $R^9$ and $R^{10}$ are the same or different and each is hydrogen or lower alkyl; $R^2$ is lower alkyl; $R^3$ is hydrogen, alkyl of 1 to 6 carbon atoms, alkenyl of 3 to 5 carbon atoms or cycloalkyl of 3 to 7 carbon atoms unsubstituted or substituted by one or two substituents selected from the group consisting of alkoxy of 1 to 4 carbon atoms, phenyl, phenoxy, benzyloxy, cycloalkyl of 3 to 7 carbon atoms, amino, alkylamino of 1 to 4 carbon atoms, alkylthio of 1 to 4 carbon atoms, pyridyl, furfuryl or tetrahydrofurfuryl; a group of the formula

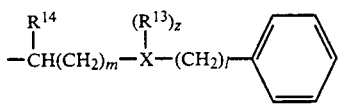

wherein X is nitrogen or oxygen; $R^{13}$ is alkyl of 1 to 4 carbon atoms; and z is 1 when X is nitrogen and when X is oxygen, z is 0; $R^{14}$ is hydrogen, alkyl of 1 to 4 carbon atoms or phenyl unsubstituted or substituted by alkyl of 1 to 4 carbon atoms; l is 0 to 2; m is 1 to 4; a group of the formula

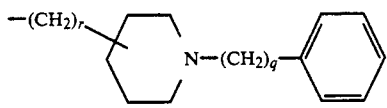

wherein q is 0 to 2 and r is 0 to 2; or a group of the formula

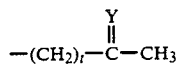

wherein t is 1 or 2 and Y is oxygen,

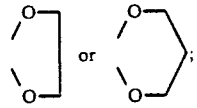

$R^4$ is alkyl of 1 to 4 carbon atoms; $R^5$ is hydrogen, nitro, cyano, trifluoromethyl, difluoromethoxy, halo, azido, alkoxycarbonyl of 1 to 4 carbon atoms, aminocarbonyl, sulfamyl or alkylsulfonyl of 1 to 4 carbon atoms; and $R^6$ is hydrogen, nitro, cyano, trifluoromethyl, difluoromethoxy, halo, azido, alkoxycarbonyl of 1 to 4 carbon atoms, aminocarbonyl, sulfamyl or alkylsulfonyl of 1 to 4 carbon atoms.

3. A compound according to claim 1 or a pharmaceutically acceptable salt thereof wherein $R^1$ is 3-oxo-2,4-dioxa-3-phosphaspiro[5.5]undecan-3-yl or 2-oxo-1,3,2-dioxaphosphorinan-2-yl unsubstituted or substituted by one or more lower alkyl moieties; $R^2$ is alkyl of 1 to 4 carbon atoms; $R^3$ is alkyl of 1 to 5 carbon atoms or 2-(N-benzyl-N-lower alkylamino)-lower alkyl; $R^4$ is alkyl of 1 to 4 carbon atoms; $R^5$ is nitro, halo, trihalomethyl or dihaloalkoxy; and $R^6$ is hydrogen or halo.

4. A compound according to claim 1 or a pharmaceutically acceptable salt thereof wherein $R^1$ is 3-oxo-2,4-dioxa- 3- phosphaspiro[5.5]undecan-3-yl or 2-oxo-1,3,2-dioxaphosphorinan-2-yl unsubstituted or substituted by one or two alkyl moieties of 1 to 3 carbon atoms; $R^2$ is methyl, ethyl, propyl or isopropyl; $R^3$ is alkyl of 1 to 4 carbon atoms or 2-(N-benzyl-N-methylamino)ethyl; $R^4$ is methyl, ethyl, propyl or isopropyl; $R^5$ is nitro, chloro, trifluoromethyl or difluoromethoxy; and $R^6$ is hydrogen or chloro.

5. A compound according to claim 1 or a pharmaceutically acceptable salt thereof wherein $R^1$ is 3-oxo-2,4-dioxa-3-phosphorinaspiro[5.5]undecan-3-yl or 2-oxo-1,3,2-dioxaphosphan-2-yl unsubstituted or substituted by methyl, ethyl or isopropyl at the 5-position; $R^2$ methyl; $R^3$ is methyl, ethyl or 2-(N-benzyl-N-methylamino)ethyl; $R^4$ is methyl; $R^5$ is nitro, chloro, trifluoromethyl or difluoromethoxy at the 2- or 3-position; and $R^6$ is hydrogen or 2-chloro.

6. A compound according to claim 1 or a pharmaceutically acceptable salt thereof wherein $R^1$ is 2-oxo-1,3,2-dioxaphosphorinan-2-yl unsubstituted or substituted by 5-methyl; $R^2$ is methyl; $R^3$ is methyl or ethyl; $R^4$ is methyl; $R^5$ is nitro or trifluoromethyl at the 2- or 3-position; and $R^6$ is hydrogen.

7. The compound according to claim 1 which is Methyl 2,6-dimethyl-4-(2-nitrophenyl)-5-(2-oxo-1,3,2-dioxaphosphorinan-2-yl)-1,4-dihydropyridine-3-carboxylate or a pharmaceutically acceptable salt thereof.

8. The compound according to claim 1 which is Ethyl 2,6-dimethyl-4-(2-nitrophenyl)-5-(2-oxo-1,3,2-dioxaphosphorinan-2-yl)-1,4-dihydropyridine-3-carboxylate or a pharmaceutically acceptable salt thereof.

9. The compound according to claim 1 which is Methyl 5-(5-methyl-2-oxo-1,3,2-dioxaphosphorinan-2-yl)-2,6-dimethyl-4-(3-nitrophenyl)-1,4-dihydropyridine-3-carboxylate or a pharmaceutically acceptable salt thereof.

10. The compound according to claim 1 which is Methyl 2,6-dimethyl-5-(2-oxo-1,3,2-dioxaphosphorinan-2-yl)-4-(2-trifluoromethylphenyl)-1,4-dihydropyridine-3-carboxylate or a pharmaceutically acceptable salt thereof.

11. The compound according to claim 1 which is 2-(N-Benzyl-N-methylamino)-ethyl 5-(5-ethyl-2-oxo-1,3,2-dioxaphosphorinan- 2-yl -2,6-dimethyl 4- 3-nitrophenyl -1,4-dihydropyridine-3-carboxylate or a pharmaceutically acceptable salt thereof.

12. The compound according to claim 1 which is Ethyl 2,6-dimethyl-4-(3-nitrophenyl)-5-(5-isopropyl-2-oxo-1,3,2-dioxaphosphorinan-2-yl)-1,4-dihydropyridine-3-carboxylate or a pharmaceutically acceptable salt thereof.

13. The compound according to claim 1 which is Ethyl 2,6-dimethyl-4-(2-nitrophenyl)-5-(3-oxo-2,4-dioxa-3-phosphaspiro(5,5)undecan-3-yl)-1,4-dihydropyridine-3-carboxylate or a pharmaceutically acceptable salt thereof.

14. The compound according to claim 1 which is 2-(N-Benzyl-N-methylamino)-ethyl 2,6-dimethyl-5-(2-oxo-1,3,2-dioxaphosphorinan-2-yl)-4-(2-trifluoromethylphenyl)-1,4-dihydropyridine-3-carboxylate or a pharmaceutically acceptable salt thereof.

15. The compound according to claim 1 which is Methyl 4-(2,3-dichlorophenyl)-2,6-dimethyl-5-(2-oxo-1,3,2-dioxaphosphorinan-2-yl)-1,4-dihydropyridine-3-carboxylate or a pharmaceutically acceptable salt thereof.

16. The compound according to claim 1 which is 2-(N-Benzyl-N-methylamino)-ethyl 2,6-dimethyl-5-(5,5-dimethyl-2-oxo-1,3,2-dioxaphosporinan-2-yl)-4-(2-trifluoromethylphenyl)-1,4-dihydropyridine-3-carboxylate or a pharmaceutically acceptable salt thereof.

17. The compound according to claim 1 which is 2-(N-Benzyl-N-methylamino)-ethyl 4-(2-difluoromethoxyphenyl)-2,6-dimethyl-5-(5,5-dimethyl-2-oxo-1,3,2-dioxaphosphorinan-2-yl)-1,4-dihydropyridine-3-carboxylate or a pharmaceutically acceptable salt thereof.

18. A compound of the formula I:

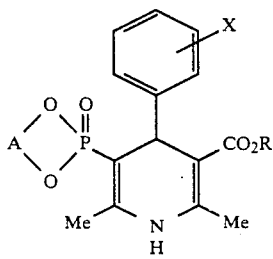

wherein
X is hydrogen, nitro, trifluoromethyl, fluorine, chlorine, bromine or iodine;
A is 1,3-propylene or 1,4-butylene which may be substituted by $C_1$–$C_3$ alkyl;
R is $C_1$–$C_4$ alkyl or —Y—N($R^1$)($R^2$) which may be the same or different and is hydrogen, $C_1$–$C_6$ alkyl, or aralkyl; and Y is $C_2$–$C_6$ alkylene; and
Me is methyl; or its pharmaceutically acceptable salt.

19. The compound of claim 18, wherein
A is 1,3-propylene or 1,4-butylene which may be substituted by one or two methyl groups, and R is

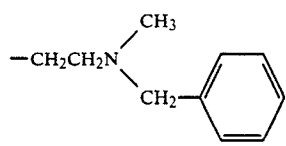

or $C_1$–$C_4$ alkyl.

20. The compound of claim 18, wherein A is

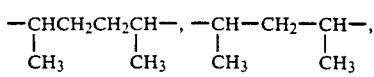

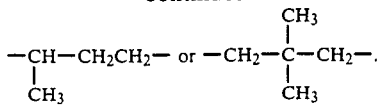

R is

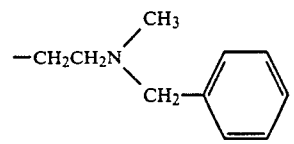

or $CH_3$; and
X is $NO_2$, $CF_3$, F, Cl, Br or I substituted at the 2- or 3- position.

21. The compound of claim 20, wherein R is

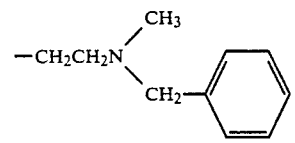

22. The compound of claim 21, wherein X is $CF_3$, $NO_2$ or Cl substituted at the 2- or 3- position.

23. A pharmaceutical composition useful for effecting vasodilation and hypotensive action in humans and animals which comprises a therapeutically effective amount of a compound of the formula (I) or a pharmaceutically acceptable salt thereof:

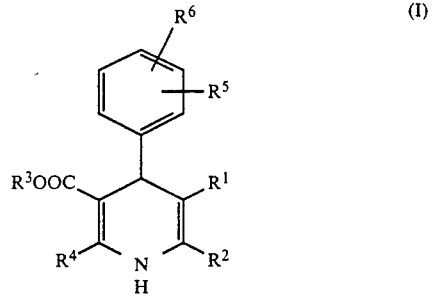

wherein $R^1$ is of the formula (II):

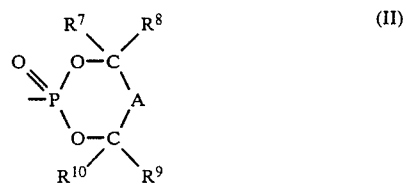

wherein A is

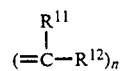

wherein n is an integer from 0 to 2 and $R^{11}$ and $R^{12}$ are the same or different and each is hydrogen, alkyl, alkoxycarbonyl, phenyl, alkoxy, alkoxyalkyl, phenoxy or aralkyloxy, or $R^{11}$ and $R^{12}$ together with the carbon atom to which they are attached form an alkylene group of 3 to 7 carbon atoms when n is 1 and when n is 2, both $R^{11}$ and $R^{12}$ are hydrogen, or two $R^{11}$ form a double bond while $R^{12}$ is hydrogen; $R^7$, $R^8$, $R^9$ and $R^{10}$ are the same or different and each is hydrogen or lower alkyl; $R^2$ is lower alkyl; $R^3$ is hydrogen; a hydrocarbon of 1 to 10 carbon atoms containing 0 to 4 unsaturated bonds unsubstituted or substituted by one or more substituents selected from the group consisting of alkoxy, aryloxy, aralkyloxy, cycloalkyl, amino, alkylamino, alkylthio, pyridyl, furfuryl and tetrahydrofurfuryl; a group of the formula

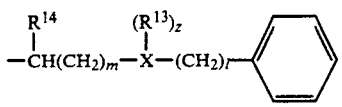

wherein X is nitrogen or oxygen; $R^{13}$ is lower alkyl or lower alkenyl and z is 1 when X is nitrogen and when X is oxygen, z is 0; $R^{14}$ is hydrogen, lower alkyl or phenyl unsubstituted or substituted by alkyl; l is an integer from 0 to 2; m is an integer from 1 to 4; a group of the formula

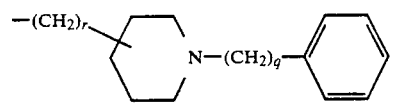

wherein q is an integer from 0 to 2 and r is an integer from 0 to 2; or a group of the formula

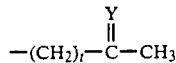

wherein t is 1 or 2 and Y is oxygen

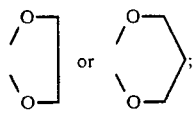

$R^4$ is lower alkyl; $R^5$ is hydrogen, nitro, cyano, trihalomethyl, dihalo-lower alkoxy, halo, azido, alkoxycarbonyl, aminocarbonyl, sulfamyl or alkylsulfonyl; and $R^6$ is hydrogen, nitro, cyano, trihalomethyl, dihalo-lower alkoxy, halo, azido, alkoxycarboryl, aminocarbonyl, sulfamyl or alkylsulfonyl, in combination with a pharmaceutically acceptable carrier.

24. A composition according to claim 23 wherein $R^{11}$ and $R^{12}$ are the same or different and each is hydrogen, lower alkyl, lower alkoxycarbonyl, phenyl, lower alkoxy, lower alkoxy lower alkyl, phenoxy or aralkyloxy wherein the alkyl moiety is of 1 to 4 carbon atoms; or $R^{11}$ and $R^{12}$ form an alkylene group together with the carbon atom to which they are attached of 3 to 7 carbon atoms when n is 1 or when n is 2, both $R^{11}$ and $R^{12}$ are hydrogen or two $R^{11}$ form a double bond and $R^{12}$ is hydrogen; $R^7$, $R^8$, $R^9$ and $R^{10}$ are the same or different and each is hydrogen or lower alkyl; $R^2$ is lower alkyl; $R^3$ is hydrogen, alkyl of 1 to 6 carbon atoms, alkenyl of 3 to 5 carbon atoms or cycloalkyl of 3 to 7 carbon atoms unsubstituted or substituted by one or two substituents selected from the group consisting of alkoxy of 1 to 4 carbon atoms, phenyl, phenoxy, benzyloxy, cycloalkyl of 3 to 7 carbon atoms, amino, alkylamino of 1 to 4 carbon atoms, alkylthio of 1 to 4 carbon atoms, pyridyl, furfuryl or tetrahydrofurfuryl; a group of the formula

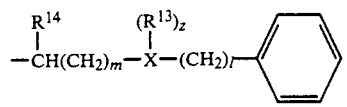

wherein X is nitrogen or oxygen; $R^{13}$ is alkyl of 1 to 4 carbon atoms; and z is 1 when X is nitrogen and when X is oxygen, z is 0; $R^{14}$ is hydrogen, alkyl of 1 to 4 carbon atoms or phenyl unsubstituted or substituted by alkyl of 1 to 4 carbon atoms; l is 0 to 2; m is 1 to 4; a group of the formula

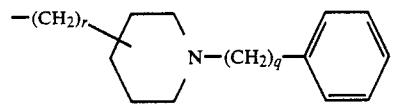

wherein q is 0 to 2 and r is 0 to 2; or a group of the formula

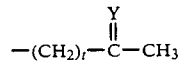

wherein t is 1 or 2; Y is oxygen,

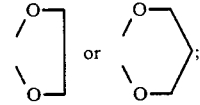

$R^4$ is alkyl of 1 to 4 carbon atoms; $R^5$ is hydrogen, nitro, cyano, trifluoromethyl, difluoromethoxy, halo, azido, alkoxycarbonyl of 1 to 4 carbon atoms, aminocarbonyl, sulfamyl or alkylsulfonyl of 1 to 4 carbon atoms; and $R^6$ is hydrogen, nitro, cyano, trifluoromethyl, difluoromethoxy, halo, azido, alkoxycarbonyl of 1 to 4 carbon atoms, aminocarbonyl, sulfamyl or alkylsulfonyl of 1 to 4 carbon atoms.

25. A composition according to claim 23 wherein $R^1$ is 3-oxo-2,4-dioxa-3-phosphorinaspiro[5.5]undecan-3-yl or 2-oxo-1,3,2-dioxaphosphan-2-yl unsubstituted or substituted by one or more lower alkyl moieties; $R^2$ is alkyl of 1 to 4 carbon atoms; $R^3$ is alkyl of 1 to 5 carbon atoms or 2-(N-benzyl-N-lower alkylamino)-lower alkyl; $R^4$ is alkyl of 1 to 4 carbon atoms; $R^5$ is nitro, halo, trihalomethyl or dihaloalkoxy; and $R^6$ is hydrogen or halo.

26. A composition according to claim 23 wherein $R^1$ is 3-oxo-2,4-dioxa-3-phosphaspiro[5.5]undecan-3-yl or 2-oxo-1,3,2-dioxaphosphorinan-2-yl unsubstituted or substituted by one or two alkyl moieties of 1 to 3 carbon atoms; $R^2$ is methyl, ethyl, propyl or isopropyl; $R^3$ is alkyl of 1 to 4 carbon atoms or 2-(N-benzyl-N-methylamino)ethyl; $R^4$ is methyl, ethyl, propyl or isopropyl; $R^5$ is nitro, chloro, trifluoromethyl or difluoromethoxy; and $R^6$ is hydrogen or chloro.

27. A composition according to claim 23 wherein $R^1$ is 3-oxo-2,4-dioxa-3-phosphaspiro[5.5]undecan-3-yl or 2-oxo-1,3,2-dioxaphosphorinan-2-yl unsubstituted or substituted by methyl, ethyl or isopropyl at the 5-position; $R^2$ methyl; $R^3$ is methyl, ethyl or 2-(N-benzyl-N-methylamino)ethyl; $R^4$ is methyl; $R^5$ is nitro, chloro, trifluoromethyl or difluoromethoxy at the 2- or 3-position; and R⁶ is hydrogen or 2-chloro.

28. A composition according to claim 23 wherein $R^1$ is 2-oxo-1,3,2-dioxaphosphorinan-2-yl unsubstituted or substituted by 5-methyl; $R^2$ is methyl; $R^3$ is methyl or ethyl; $R^4$ is methyl; $R^5$ is nitro or trifluoromethyl at the 2- or 3-position; and $R^6$ is hydrogen.

29. A composition according to claim 23 wherein the compound is Methyl 2,6-dimethyl-4-(2-nitrophenyl)-5-(2-oxo-1,3,2-dioxaphosphorinan-2-yl)-1,4-dihydropyridine-3-carboxylate or a pharmaceutically acceptable salt thereof.

30. A composition according to claim 23 wherein the compound is Ethyl 2,6- dimethyl-4-(2-nitrophenyl)-5-(2-oxo-1,3,2-dioxaphosphorinan-2-yl)-1,4-dihydropyridine-3-carboxylate or a pharmaceutically acceptable salt thereof.

31. A composition according to claim 23 wherein the compound is Methyl 5-(5-methyl- 2-oxo-1,3,2-dioxaphosphorinan-2-yl)-2,6-dimethyl-4-(3-nitrophenyl)-1,4-dihydropyridine-3-carboxylate or a pharmaceutically acceptable salt thereof.

32. A composition according to claim 23 wherein the compound is Methyl 2,6- dimethyl-5-(2-oxo-1,3,2-dioxaphosphorinan-2-yl)-4-(2-trifluoromethylphenyl)-1,4-dihydropyridine-3-carboxylate or a pharmaceutically acceptable salt thereof.

33. A composition according to claim 23 wherein the compound is 2-(N-Benzyl-N-methylamino)-ethyl 5-(5-ethyl-2-oxo-1,3,2-dioxa-phosphorinan-2-yl)-2,6-dimethyl-4-(3-nitrophenyl)-1,4-dihydro-pyridine-3-carboxylate or a pharmaceutically acceptable salt thereof.

34. A composition according to claim 23 wherein the compound is Ethyl 2,6- dimethyl-4-(3- nitrophenyl)-5-(5-isopropyl-2-oxo-1,3,2-dioxa-phosphorinan-2-yl)-1,4-dihydropyridine- 3-carboxylate or a pharmaceutically acceptable salt thereof.

35. A composition according to claim 23 wherein the compound is Ethyl 2,6- dimethyl-4- (2-nitrophenyl)-5-(3-oxo-2,4-dioxa-3-phosphaspiro-(5,5)undecan-3-yl)-1,4-dihydropyridine-3-carboxylate or a pharmaceutically acceptable salt thereof.

36. A composition according to claim 23 wherein the compound is 2-(N-Benzyl-N-methylamino)-ethyl 2,6-dimethyl-5-(2-oxo-1,3,2-dioxaphosphorinan-2-yl)-4-(2-trifluoromethylphenyl)-1,4-dihydro-pyridine-3-carboxylate or a pharmaceutically acceptable salt thereof.

37. A composition according to claim 23 wherein the compound is Methyl 4-(2,3-dichlorophenyl)-2,6-dimethyl-5-(2-oxo-1,3,2-dioxa-phosphorinan-2-yl)-1,4-dihydropyridine-(3-carboxylate or a pharmaceutically acceptable salt thereof.

38. A composition according to claim 23 wherein the compound is 2-(N-Benzyl-N-methylamino)-ethyl 2,6-dimethyl-5-(5,5-dimethyl-2-oxo-1,3,2-dioxaphosporinan-2-yl)-4-(2-trifluoromethylphenyl)-1,4-dihydropyridine-3-carboxylate or a pharmaceutically acceptable salt thereof.

39. A composition according to claim 23 wherein the compound is 2-(N-Benzyl-N-methylamino)-ethyl 4-(2-difluoromethoxyphenyl)-2,6-dimethyl-5-(5,5-dimethyl-2-oxo-1,3,2-dioxaphosphorinan-2-yl)-1,4-dihydropyridine-3-carboxylate or a pharmaceutically acceptable salt thereof.

40. An antihypertensive, coronary or peripheral vasodilator composition comprising (a) an antihypertensive, coronary or peripheral vasodilator effective amount of the compound of claim 18; and (b) a pharmaceutically acceptable diluent or carrier.

41. A method of effecting vasodilation or hypotensive action in humans and animals which comprises administering to a human or animal in need thereof a therapeutically effective amount of a compound of the formula (I):

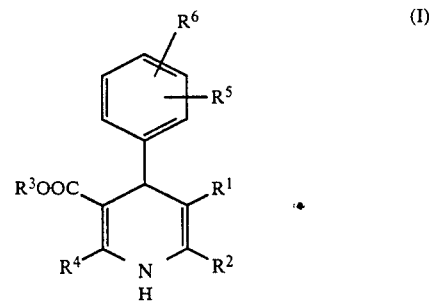

wherein $R^1$ is of the formula (II):

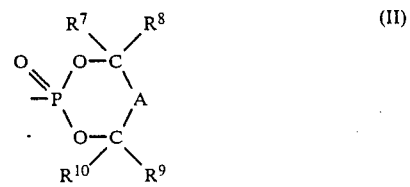

wherein A is

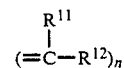

wherein n is an integer from 0 to 2 and $R^{11}$ and $R^{12}$ are the same or different and each is hydrogen, alkyl, alkoxycarbonyl, phenyl, alkoxy, alkoxyalkyl, phenoxy or aralkyloxy, or $R^{11}$ and $R^{12}$ together with the carbon atom to which they are attached form an alkylene group of 3 to 7 carbon atoms when n is 1 and when n is 2, both $R^{11}$ and $R^{12}$ are hydrogen, or two $R^{11}$ form a double bond while $R^{12}$ is hydrogen; $R^7, R^8$, $R^9$ and $R^{10}$ are the same or different and each is hydrogen or lower alkyl; $R^2$ is lower alkyl; $R^3$ is hydrogen; a hydrocarbon of 1 to 10 carbon atoms containing 0 to 4 unsaturated bonds unsubstituted or substituted by one or more substituents selected from the group consisting of alkoxy, aryl, aryloxy, aralkyloxy, cycloalkyl, amino, alkylamino, alkylthio, pyridyl, furfuryl and tetrahydrofurfuryl; a group of the formula

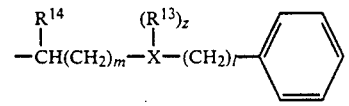

wherein X is nitrogen or oxygen; $R^{13}$ is lower alkyl or lower alkenyl and z is 1 when X is nitrogen and when X is oxygen, z is 0; $R^{14}$ is hydrogen, lower alkyl or phenyl unsubstituted or substituted by alkyl; l is an integer from 0 to 2; m is an integer from 1 to 4; a group of the formula

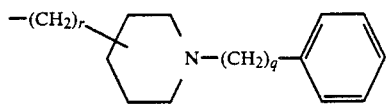

wherein q is an integer from 0 to 2 and r is an integer from 0 to 2; or a group of the formula

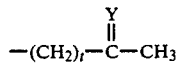

wherein t is 1 or 2 and Y is oxygen

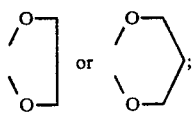

$R^4$ is lower alkyl; $R^5$ is hydrogen, nitro, cyano, trihalomethyl, dihalo-lower alkoxy, halo, azido, alkoxycarbonyl, aminocarbonyl, sulfamyl or alkylsulfonyl; and $R^6$ is hydrogen, nitro, cyano, trihalomethyl, dihalo-lower alkoxy, halo, azido, alkoxycarbonyl, aminocarbonyl, sulfamyl or alkylsulfonyl, in combination with a pharmaceutically acceptable carrier.

42. A method according to claim 41 wherein $R^{11}$ and $R^{12}$ are the same or different and each is hydrogen, lower alkyl, lower alkoxycarbonyl, phenyl, lower alkoxy, lower alkoxy lower alkyl, phenoxy or aralkyloxy wherein the alkyl moiety is of 1 to 4 carbon atoms; or $R^{11}$ and $R^{12}$ form an alkylene group together with the carbon atom to which they are attached of 3 to 7 carbon atoms when n is 1 or when n is 2, both $R^{11}$ and $R^{12}$ are hydrogen or two $R^{11}$ form a double bond and $R^{12}$ is hydrogen; $R^7, R^8, R^9$ and $R^{10}$ are the same or different and each is hydrogen or lower alkyl; $R^2$ is lower alkyl; $R^3$ is hydrogen, alkyl of 1 to 6 carbon atoms, alkenyl of 3 to 5 carbon atoms or cycloalkyl of 3 to 7 carbon atoms unsubstituted or substituted by one or two substituents selected from the group consisting of alkoxy of 1 to 4 carbon atoms, phenyl, phenoxy, benzyloxy, cycloalkyl of 3 to 7 carbon atoms, amino, alkylamino of 1 to 4 carbon atoms, alkylthio of 1 to 4 carbon atoms, pyridyl, furfuryl or tetrahydrofurfuryl., a group of the formula

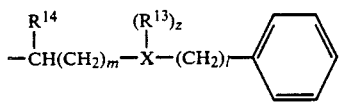

wherein X is nitrogen or oxygen; $R^{13}$ is alkyl of 1 to 4 carbon atoms; and Z is 1 when X is nitrogen and when X is oxygen, Z is 0; $R^{14}$ is hydrogen, alkyl of 1 to 4 carbon atoms or phenyl unsubstituted or substituted by alkyl of 1 to 4 carbon atoms; is 0 to 2; m is 1 to 4; a group of the formula

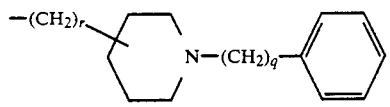

wherein q is 0 to 2 and r is 0 to 2; or a group of the formula

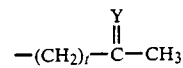

wherein t is 1 or 2; Y is oxygen,

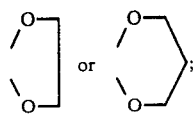

$R^4$ is alkyl of 1 to 4 carbon atoms; $R^5$ is hydrogen, nitro, cyano, trifluoromethyl, difluoromethoxy, halo, azido, alkoxycarbonyl of 1 to 4 carbon atoms, aminocarbonyl, sulfamyl or alkylsulfonyl of 1 to 4 carbon atoms; and $R^6$ is hydrogen, nitro, cyano, trifluoromethyl, difluoromethoxy, halo, azido, alkoxycarbonyl of 1 to 4 carbon atoms, aminocarbonyl, sulfamyl or alkylsulfonyl of 1 to 4 carbon atoms.

43. A method according to claim 36 wherein $R^1$ is 3-oxo-2,4- dioxa-3-phosphaspiro[5.5]undecan-3-yl or 2-oxo-1,3,2-dioxaphosphorinan-2-yl unsubstituted or substituted by one or more lower alkyl moieties; $R^2$ is alkyl of 1 to 4 carbon atoms; $R^3$ is alkyl of 1 to 5 carbon atoms or 2-(N-benzyl-N-lower alkylamino)-lower alkyl; $R^4$ is alkyl of 1 to 4 carbon atoms; $R^5$ is nitro, halo, trihalomethyl or dihaloalkoxy; and $R^6$ is hydrogen or halo.

44. A method according to claim 41 wherein $R^1$ is 3-oxo-2,4-dioxa-3-phosphaspiro[5 .5]undecan-3-yl or 2-oxo-1,3,2-dioxaphosphorinan-2-yl unsubstituted or substituted by one or two alkyl moieties of 1 to 3 carbon atoms; $R^2$ is methyl, ethyl, propyl or isopropyl; $R^3$ is alkyl of 1 to 4 carbon atoms or 2-(N-benzyl-N-methylamino)ethyl; $R^4$ is methyl, ethyl, propyl or isopropyl; $R^5$ is nitro, chloro, trifluoromethyl or difluoromethoxy; and $R^6$ is hydrogen or chloro.

45. A method according to claim 41 wherein $R^1$ is 3-oxo-2 ,4-dioxa- 3- phosphaspiro[5.5]undecan- 3-yl or 2-oxo-1,3,2-dioxaphosphorinan-2-yl unsubstituted or substituted by methyl, ethyl or isopropyl at the 5-position; $R^2$ methyl; $R^3$ is methyl, ethyl or 2-(N-benzyl-N-methylamino)ethyl $R^4$ is methyl; $R^5$ is nitro, chloro, trifluoromethyl or difluoromethoxy at the 2- or 3-position; and $R^6$ is hydrogen or 2-chloro.

46. A method according to claim 41 wherein $R^1$ is 2-oxo-1,3,2-dioxaphosphorinan-2-yl unsubstituted or substituted by 5-methyl; $R^2$ is methyl; $R^3$ is methyl or ethyl; $R^4$ is methyl; $R^5$ is nitro or trifluoromethyl at the 2- or 3-position; and $R^6$ is hydrogen.

47. A method according to claim 41 wherein the compound is Methyl 2,6-dimethyl-4-(2-nitrophenyl)-5-(2-oxo-1,3,2-dioxaphosphorinan-2-yl)-1,4-dihydropyridine-3-carboxylate or a pharmaceutically acceptable salt thereof.

48. A method according to claim 41 wherein the compound is Ethyl 2,6-dimethyl-4-(2-nitrophenyl)-5-(2-oxo-1,3,2-dioxaphosphorinan-2-yl)-1,4-dihydropyridine-3-carboxylate or a pharmaceutically acceptable salt thereof.

49. A method according to claim 41 wherein the compound is Methyl 5-(5-methyl-2-oxo-1,3,2-dioxaphosphorinan-2-yl)-2,6-dimethyl-4-(3-nitrophenyl)-1,4-dihydropyridine-3-carboxylate or a pharmaceutically acceptable salt thereof.

50. A method according to claim 41 wherein the compound is Methyl 2,6-dimethyl-5-(2-oxo1,3,2-dioxaphosphorinan-2-yl)-4-(2-trifluoromethylphenyl)-1,4-dihydropyridine-3-carboxylate or a pharmaceutically acceptable salt thereof.

51. A method according to claim 41 wherein the compound is 2-(N-Benzyl-N-methylamino)-ethyl 5-(5-ethyl-2-oxo-1,3,2-dioxa-phosphorinan-2-yl)-2,6-dimethyl-4-(3-nitrophenyl)-1,4-dihydro-pyridine-3-carboxylate or a pharmaceutically acceptable salt thereof.

52. A method according to claim 41 wherein the compound is Ethyl 2,6-dimethyl-4-(3-nitrophenyl)-5-(5-isopropyl-2-oxo-1,3,2-dioxa-phosphorinan-2-yl)-1,4-dihydropyridine-3-carboxylate or a pharmaceutically acceptable salt thereof.

53. A method according to claim 41 wherein the compound is Ethyl 2,6-dimethyl-4-(2-nitrophenyl)-5-(3-oxo-2,4-dioxa-3-phosphaspiro-(5,5)undecan-3-yl),1,4-dihydropyridine-3-carboxylate or a pharmaceutically acceptable salt thereof.

54. A method according to claim 41 wherein the compound is 2-(N-Benzyl-N-methylamino)-ethyl 2,6-dimethyl-5-(2-oxo-1,3,2-dioxaphosphorinan-2-yl)-4-(2-trifluoromethylphenyl)-1,4-dihydro-pyridine-3-carboxylate or a pharmaceutically acceptable salt thereof.

55. A method according to claim 41 wherein the compound is Methyl 4-(2,3-dichlorophenyl)2,6-dimethyl-5-(2-oxo-1,3,2-dioxa-phosphorinan-2-yl)-1,4-dihydropyridine-3-carboxylate or a pharmaceutically acceptable salt thereof.

56. A method according to claim 41 wherein the compound is 2-(N-Benzyl-N-methylamino)-ethyl 2,6-dimethyl-5-(5,5-dimethyl-2-oxo-1,3,2-dioxaphosphorinan-2-yl)-4-(2-trifluoromethylphenyl)-1,4-dihydropyridine-3-carboxylate or a pharmaceutically acceptable salt thereof.

57. A method according to claim 41 wherein the compound is 2-(N-Benzyl-N-methylamino)-ethyl 4-(2-difluoromethoxyphenyl)-2,6-dimethyl-5-(5,5-dimethyl-2-oxo-1,3,2-dioxaposphorinan-2-yl)-1,4-dihydropyridine-3-carboxylate or a pharmaceutically acceptable salt thereof.

58. A method of treating hypertension in a subject in need of such treatment comprising administering to the subject an antihypertensive effective amount of the compound of the formula I as defined in claim 18 to produce such effect.

59. A method of producing coronary vasodilation in a patient in need of such treatment comprising administering to the patient a coronary vasodilating effective amount of the compound of claim 18 to produce such effect.

60. A method of producing peripheral vasodilation in a patient in need of such treatment comprising administering to the patient a peripheral vasodilating effective amount of the compound of claim 18 to produce such effect.

* * * * *